US010253085B2

(12) United States Patent
Caligiuri et al.

(10) Patent No.: US 10,253,085 B2
(45) Date of Patent: *Apr. 9, 2019

(54) CD31 PEPTIDES FOR THE TREATMENT OF THROMBOTIC OR AUTOIMMUNE DISORDERS

(71) Applicants: Giuseppina Caligiuri, Paris (FR); Antonino Nicoletti, Paris (FR)

(72) Inventors: Giuseppina Caligiuri, Paris (FR); Antonino Nicoletti, Paris (FR)

(73) Assignee: INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 412 days.

This patent is subject to a terminal disclaimer.

(21) Appl. No.: 14/809,603

(22) Filed: Jul. 27, 2015

(65) Prior Publication Data

US 2015/0376258 A1    Dec. 31, 2015

Related U.S. Application Data

(62) Division of application No. 13/001,513, filed as application No. PCT/EP2009/058188 on Jun. 30, 2009, now Pat. No. 9,127,086.

(30) Foreign Application Priority Data

Jun. 30, 2008 (EP) .................................... 08305360

(51) Int. Cl.
| | |
|---|---|
| *A61K 38/03* | (2006.01) |
| *C07K 4/00* | (2006.01) |
| *C07K 7/00* | (2006.01) |
| *C07K 14/705* | (2006.01) |
| *G01N 33/50* | (2006.01) |
| *A61K 38/00* | (2006.01) |

(52) U.S. Cl.
CPC ..... *C07K 14/70503* (2013.01); *G01N 33/505* (2013.01); *A61K 38/00* (2013.01); *G01N 2333/70596* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 6,087,331 A | 7/2000 | Newman et al. | |
| 9,127,086 B2 * | 9/2015 | Caligiuri .......... | C07K 14/70503 |
| 2006/0099635 A1 | 5/2006 | Ling et al. | |
| 2008/0044900 A1 | 2/2008 | Mooney et al. | |

OTHER PUBLICATIONS

Sato et al.; "Clinical Significance of Soluble CD31 in Patients with Systemic Sclerosis (SSc): Association with Limited Cutaneous SSc"; The Journal of Rheumatology, 2001, pp. 2460-2465.
Chen et al.; "Administration of a CD31-Derived Peptide Delays the Onset and Significantly Increases Survival From Lethal Graft-Versus-Host Disease"; Blood Journal, vol. 89, No. 4, Feb. 15, 1997; pp. 1452-1459.
Zehnder et al.; "Involvement of CD31 in Lymphocyte-Mediated Immune Responses: Importance of the Membrane-Proximal Immunoglobulin Domain and Identification of an Inhibiting CD31 Peptide"; Blood Journal, vol. 85, No. 5, Mar. 1, 1995; pp. 1282-1288.
Kalinowska et al.; PECAM-1, A Key Player in Neuroinflammation; European Journal of Neurology, vol. 13, 2006, pp. 1284-1290.
Woodfin et al.; "PECAM-1: A Multi-Functional Molecule in Inflammation and Vascular Biology"; Arterioscler Thromb Vasc Biol, Dec. 2007; pp. 2514-2523.
Reinke et al..; "Short-Term sPECAM-Fc Treatment Ameliorates EAE While Chronic Use Hastens Onset of Symptoms"; Journal of Neuroimmunology, vol. 186, 2007, pp. 86-93.
Liao et al.; "Transgenic Mice Expressing Different Levels of Soluble Platelet/Endothelial Cell Adhesion Molecule-IgG Display Distinct Inflammatory Phenotypes"; The Journal of Immunology, 1999, pp. 5640-5648.
Liao et al.; "Soluble Domain 1 of Platelet-Endothelial Cell Adhesion Molecule (PECAM) is Sufficient to Block Transendothelial Migration In Vitro and In Vivo"; J. Exp. Med. The Rockefeller University Press, vol. 185, No. 7, Apr. 7, 1997, pp. 1349-1357.
Attwood; "The Babel of Bioinformatics"; Science 290; 471-473, 2000.
Skolnick et al.; "From genes to protein structure and function: novel applications of computational approaches in the genomic era"; Trends in Biotech. 18:34-39, 2000.

* cited by examiner

*Primary Examiner* — Phillip Gambel
(74) *Attorney, Agent, or Firm* — W&C IP

(57) ABSTRACT

The present invention stems from the finding that the extracellular domain of CD31 proteins present on blood leukocytes is shed and released in the circulation as a soluble form of CD31. The invention relates to peptides corresponding to fragments of CD31 that inhibit T-cell response, and to their use in the treatment of thrombotic disorders such as atherothrombosis and autoimmune disorders.

13 Claims, 8 Drawing Sheets

Specification includes a Sequence Listing.

```
HUMAN    MQPRWAQGATMWLGVLLTLLLCSSLEGQENSFTINSVDMKSLPDWTVQNGKNLTLQCFAD  60
MOUSE    ----------MLLALGLTLVLYASLQAEENSFTINSIHMESLPSWEVMNGQQLTLECLVD  50
BOVIN    MQLRWTQRGMMWLGALLTLLLCSSLKGQENSFTINSIHMQILPHSTVQNGENLTLQCLVD  60
PIG      MRLRWTQGGNMWLGVLLTLQLCSSLEGQENSFTINSIHMEMLPGQEVHNGENLTLQCIVD  60

HUMAN    VSTTSHVKPQHQMLFYKDDVLFYNISSMKSTESYFIPFVRIYDSGTYKCTVIVNNKEKTT  120
MOUSE    ISTTSKSRSQHPVLFYKDDAMVHVTSREHTESYVIPQARVEHSGKYKCTVMLNNKEKTT  110
BOVIN    VSTTSRVKPLHQVLFYKDDVLLHNVSSRRNTESYLIPEVRVCDSGRYKCKVILNNKEKTT  120
PIG      VSTTSSVKPQHQVLFYKDLVLFHNVSSTKNTESYFISEARVYNSGRYKCTVILNNKEKTT  120

HUMAN    AEYQLLVEGVPSPPVTLDKKEAIQGGIVRVNCSVPEEKAPIHFTIEKIELNEKMVKLKRE  180
MOUSE    IEYEVKVIGVSKPKVTLDKKEVTEGGVVTVNCSLQEEKPPIFFKIEKLEVGTKVKRRID  170
BOVIN    PEYEVVVKGVSDPRVTLDKKEVIEGGVVVVNCSVPEEKAPVHFTIEKFELNIRGAKKKRE  180
PIG      AEYKVVVEGVSNPKVTLDKKEVIEGGVVKVTCSVPEEKPPVHFIIEKFELNVRDVKQRRE  180

HUMAN    KNSRDQNFVILEFPVEEQDRVLSFRCQARIISGIHMQTSESTKSELVTVTESFSTPKFHI  240
MOUSE    KTS-NENFVLMEFPIEAQDHVLVFRCQAGTLSGFKLQESEPIRSFYVTVQESFSTPKFBI  229
BOVIN    KTSQNQNFVTLEFTVEEQDRTIRFQCQAKIFSGSNVESSRPIQSDLVTVRESFSNPKFHI  240
PIG      KTANNQNSVTLEFTVEEQDRVILFSCQANVIFGTRVEISDSVRSDLVTVRESFSNPKFHI  240

HUMAN    SPTGHTMEGAQLHIKCTIQVTHLAQSFPEIIQKDKAIVAHKRHGNKAVYSVMAMVEHSG  300
MOUSE    KPPGMIIEGDQLHIRCIVQVTHLVQEFPEIIQKDKAIVATSKQSSEAVYSVMAMVEYSG  289
BOVIN    IPEGKVMEGDDLQVKCTVQVTHQAQSFPEIIQKDREIVAHNSLSSEAVYSVMATTEHNG  300
PIG      SPKGVTIEGDQLLIKCTIQVTHQAQSFPEIIQKDKEIVAHSRNGSEAVYSVMATVEHNS  300

HUMAN    NYTCKVESSRISKVSSIVVNITELFSKPELESSFTHLDQGERLNLSCSIPGAPP-ANFTI  359
MOUSE    HYTCKVESNRISKASSIKVNITELFPKPKLEFSSSRLDQGELLDLSCSVSGTPV-ANFTI  348
BOVIN    NYTCKVEASRISKVSSVVVNVTELFSKPKLESSATHLDQGEDLNLLCSIPGAPP-ANFTI  359
PIG      NYTCKVEASRISKVSSIKVNITELFSRPKLKSSATRLDQGESLRLWCSIPGAPPEANFTI  360

HUMAN    QKEDTIVSQTQDFTKIASKSDSGTYICTAGIDKVVKKSNTVQIVVCEMLSQPRISYDAQF  419
MOUSE    QKEFTVLSQYQNFSKIAFESDSGEYSCPACIGKVVKRSGLVPIQVCEMLSKPSIFHDAKS  408
BOVIN    QKGGMTVSQTQNFTKPVSEWDSGLYTCVAGVGRVFKRSNTVQITVCEMLSKPSIFHDSES  419
PIG      QKGGMMMLQDQNLTKVASEPDSGTYTCVAGIGKVVKRSNEVQIAVCEMLSKPSIFHDSGS  420

HUMAN    EVIKGQTIEVRCESISGTLPISYQLLKTSKVLENSTKNSNDPAVFKDNPTEDVEYQCVAD  479
MOUSE    EIIKGHAIGISCQSENGIAPITYHLMKQAKSDFQTLEVTSNDPATFTDKPTRDMEYQCRAD  468
BOVIN    EVIKGQTIEVSCQSVNGTAPIFVQLSNTSKPVANQSVGSNKPAIFRVKFTKDVEYCCSAD  479
PIG      EVIKGQTIEVSCQSINGTSPISYQLLKGSDLLASQHVSSNEPAVFKDNPTKDVEYQCIAD  480

HUMAN    NCHSHAKMLSEVLRVKVIAPVDEVQISTLSSKVVESGEDIVLQCAVNEGSGPITYKFYRE  539
MOUSE    NCHSHPAVFSEILPVRVIAPVDEVVISTLSSNEVQSGSEMVLRCSVKEGTSPITFQFYKE  528
BOVIN    NCHSHSKMFSEVLRVKVIAPVDEAQL-VVLKGEVEPGEFIVFYCSVNEGSFPITYKFYKE  538
PIG      NCHSHAGMPSKVLKVKVIAPVEEVKLSILLSEEVESGQAIVLQCSVKEGSGPITYKFYKE  540

HUMAN    KEGKPFYQMTSNATQAFWTKQKASKEQEGEYYCTAFNRA NHHASSVPRSKILTVRVILAPW 599
MOUSE    KEDRPFHQAVVNDTQAFWHNKQASKKQEGQYYCTASNRA SSMRTSPRSSTLAVRVPLAPW 588
BOVIN    KESKFFYQDTINATQIMWHKTTASKEYEGQYYCTASNRA NLSKHVIQSNTLTVRVYL-PL 597
PIG      KENKPFHQVTLNDTQAIWHKPKASKDQEGQYYCLASNRA TPSKNFLQSNILAVRVYLAPW 600

HUMAN    KK GLIAVVIIGVTIALLIIAAKCYFLRKAKAKQMPVEMSRPAVPLLNSNKEK-MSDPNME 658
MOUSE    KK GLIAVVVIGVVIATLIVAAKCYFLRKAKAKQKPVEMSRPAAPLLNSNSEK-ISEPSVE 647
BOVIN    FK GLIAVVVIGVITVILVLGAKCYFLKKAKAKQMPVEMSRPAVPLLNSNKEKTLSDAGTE 657
PIG      KK GLIAVVVIAVIIAVILLGAPFYFIKKSKAKQMPVEMCRPAAPLLNSNNEKTLSDPNTE 660
```

FIG.1a

```
HUMAN   ANSHYGHNDDVRNHAMKPINDNKEPLNSDVQYTEVQVSSAESHKDLGKKD--TETVYSEV 716
MOUSE   ANSHYGYDDVSGNDAVKPINQNKDPQKMDVEYTEVEVSSLEPHQALGTRA--TETVYSEI 705
BOVIN   ADRHYGYNEDVGNHAMKPLNENKEPLTLDVEYTEVEVTSPEPHQGLGTKCTETETVYSEI 717
PIG     ANRHYGYNEDVGNHAMKPLNENKEPLTLDVEYTEVEVTSPEPHRGLGTKG--TETVYSEI 718

HUMAN   RKAVPDAVESRYSRTEGSLDGT 738
MOUSE   RKVDPNLMENRYSRTEGSLNGT 727
BOVIN   RKADPDFVENRYSRTEGSLDGS 739
PIG     RKADPDLVENRYSRTEGSLDGT 740
```

FIG.1b

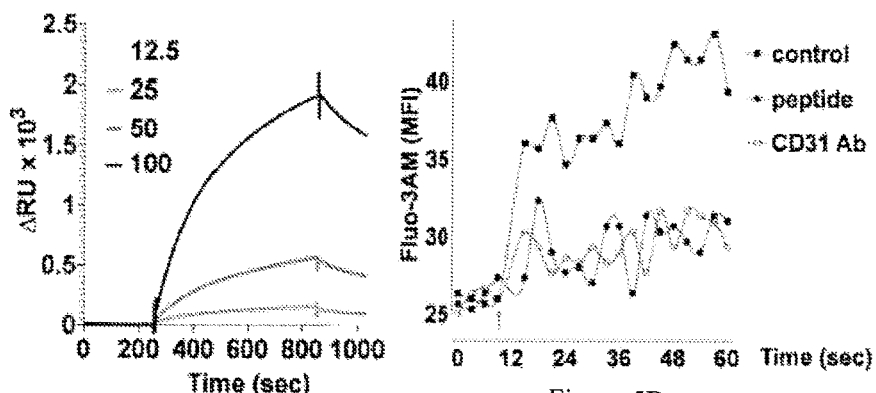
Figure 5A
Figure 5B
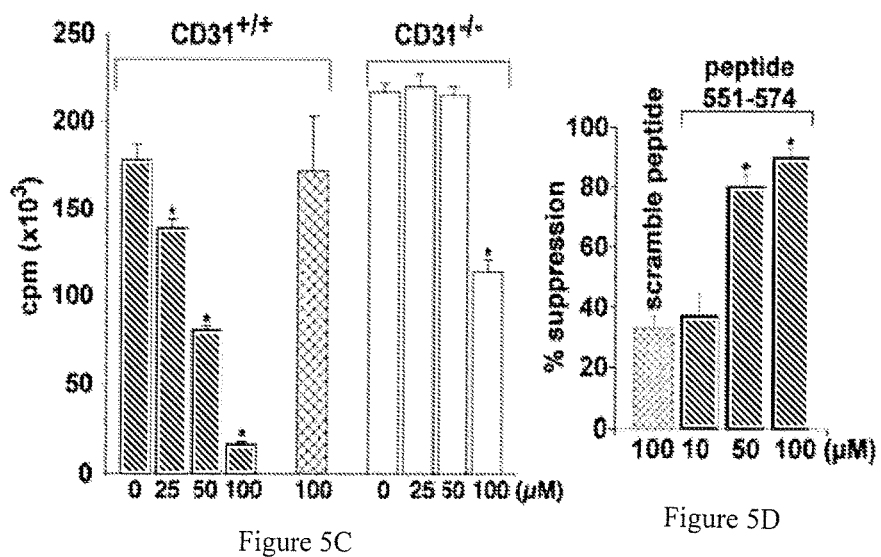
Figure 5C
Figure 5D

CD31 PEPTIDES FOR THE TREATMENT OF THROMBOTIC OR AUTOIMMUNE DISORDERS

CROSS-REFERENCE TO RELATED APPLICATIONS

This application is a divisional application of U.S. Ser. No. 13/001,513, now U.S. Pat. No. 9,127,086, which itself was a national stage filing under Rule 371 from international application PCT/EP2009/058188 filed Jun. 30, 2009, which claimed priority to an application filed with the European Union Office of Harmonization having application Ser. No. 08/305,360.3, filed Jun. 30, 2008.

FIELD OF THE INVENTION

The present invention stems from the finding that the extracellular domain of CD31 proteins present on blood leukocytes is shed and released in the circulation as a soluble form of CD31. The invention relates to peptides corresponding to fragments of CD31 that inhibit T-cell response, and to their use in the treatment of thrombotic and autoimmune disorders.

BACKGROUND

Thrombotic Disorders

In a healthy person, a homeostatic balance exists between procoagulant (clotting) forces and anticoagulant and fibrinolytic forces. Numerous genetic, acquired, and environmental factors can tip the balance in favor of coagulation, leading to the pathologic formation of thrombi in veins (e.g. deep vein thrombosis), arteries (e.g. atherothrombosis, myocardial infarction, ischemic stroke), or cardiac chambers. Thrombi can obstruct blood flow at the site of formation or detach and embolize to block a distant blood vessel (e.g. pulmonary embolism, stroke).

Accumulating evidences show that atherothrombosis, a world-leading life-threatening disease, is linked to a defective immunoregulation driving a pathologic activation of blood leukocytes and a destructive inflammatory response within the vascular wall. Consequently, a restoration of immunoregulation at the blood-vessel interface would represent an innovative therapeutic option to fight atherothrombosis.

Autoimmune Disorders

In autoimmune disorders, the immune system produces antibodies to an endogenous antigen. Antibody-coated cells, like any similarly coated foreign particle, activate the complement system, resulting in tissue injury. Autoimmune disorders include systemic lupus erythematosus (SLE), rheumatoid arthritis (RA), multiple sclerosis (MS), inflammatory bowel disease (IBD), Graves' disease and diabetes mellitus.

Several mechanisms may account for the body's attack on itself. Autoantigens may become immunogenic because they are altered chemically, physically, or biologically. Certain chemicals couple with body proteins, making them immunogenic (as in contact dermatitis). Drugs can produce several autoimmune reactions by binding covalently to serum or tissue proteins (see below). Photosensitivity exemplifies physically induced autoallergy: Ultraviolet light alters skin protein, to which the patient becomes allergic. In animal models, persistent infection with an RNA virus that combines with host tissues alters autoantigens biologically, resulting in an autoallergic disorder resembling SLE.

Most human autoimmune diseases are specific antigen-driven T-cell diseases. T-cell clones responding to specific antigenic epitopes are responsible for the initiation and/or the propagation of these diseases. Similarly, specific antigen-driven T-cell responses are responsible for the rejection of organ allografts and the immune response to tumors. Activated T cells provide the "engine" for the chronic inflammation that is associated with autoimmune diseases, organ graft rejection and tumor immunity.

CD31 (PECAM-1)

Immune responses can be controlled by inhibitory immune receptors among which CD31 (PECAM-1), which is expressed exclusively and constitutively on cells at the blood-vessel interface.

CD31 consists of a single chain molecule comprising six Ig-like extracellular domains, a short transmembrane segment and a cytoplasmic tail containing two ImmunoTyrosine-based Inhibitory Motif (ITIM)s. The structure of CD31 is shown in the table below.

| Domain | Position on SEQ ID No: 1 |
| --- | --- |
| Signal peptide | 1 to 27 |
| Extracellular domain | 28 to 601 |
| First Ig-like extracellular domain | 34 to 121 |
| Second Ig-like extracellular domain | 145 to 233 |
| Third Ig-like extracellular domain | 236 to 315 |
| Fourth Ig-like extracellular domain | 328 to 401 |
| Fifth Ig-like extracellular domain | 424 to 493 |
| Sixth Ig-like extracellular domain | 499 to 591 |
| Juxta-membrane domain | 592 to 601 |
| Transmembrane domain | 602 to 620 |
| Cytoplasmic domain | 621 to 738 |

The immunoregulatory properties of CD31 are supported by the fact that CD31 signalling drives mutual repulsion of blood leukocytes and modulates the balance between inhibitory and stimulatory signals of both innate and adaptive immune cells. Mechanical engagement of the distal Ig-like extracellular domains of CD31 induces outside-in inhibitory signalling triggered by the phosphorylation of its ITIMs, and the recruitment and activation of SH2-containing phosphatases.

Zehnder et al. (1995, Blood. 85(5):1282-8) identified a CD31 antibody that inhibited the mixed lymphocyte reaction (MLR) in a specific and dose-dependent manner. They further found that a CD31 peptide corresponding to the epitope of this antibody, i.e. to the 23 membrane-proximal amino acids of CD31, strongly inhibited the MLR. They hypothesized that the 23 membrane-proximal amino acids of CD31 constitutes a functionally important region, and that the CD31 peptide interferes with lymphocyte activation by competing for binding epitopes. However, Zehnder et al. failed to teach whether CD31-mediated signaling is activated or inhibited by the CD31 peptide.

Chen et al. (1997, Blood. 89(4):1452-9) showed that this peptide delayed onset of graft-versus-host disease (GVHD) and increased long-term survival in a murine model of the disease. They hypothesized that the CD31 peptide inhibits a common pathway in T-cell activation. Again, Chen et al. failed to elucidate the role played by the CD31 peptide in T-cell activation. In particular, these previous works did not assess the putative effect of the peptide on the CD31 signaling cascade and more precisely on the phosporylation state of the CD31 ITIMs.

By a yet unknown mechanism, CD31 is "lost" on certain circulating lymphocytes. Its loss is observed upon lymphocyte activation and it has been recently shown that the absence of lymphocyte CD31 signalling, in turn, heightens the pathologic immune responses involved in the development of atherothrombosis.

A soluble form of CD31, due to a variant transcript lacking the transmembrane segment, has also been reported and therefore it is currently thought that the individual amount of circulating CD31 is genetically determined. Consequently, a number of previous studies have attempted to find a correlation between plasma levels of soluble CD31 and the risk of atherothrombosis or other autoimmune diseases. However, independently of the specific genetic polymorphisms analyzed, data showed a broad range of plasma CD31 values and the results of these different studies were contradicting.

There is therefore a need for better understanding the biological function of CD31. This would allow the provision of more efficient therapeutics for the treatment of diseases linked with T-cell activation.

DESCRIPTION OF THE INVENTION

It has surprisingly been found that the assumed loss of CD31 on activated/memory T lymphocytes is actually incomplete and results from shedding of CD31 between the $5^{th}$ and the $6^{th}$ extracellular Ig-like domains. The shed extracellular domain of CD31 (further referred to as "shed CD31") is then released into the circulation, where it is present together with a soluble splice variant of CD31.

In addition, it has been shown that a high risk of atherothrombosis is linked with the increase in shed CD31 and decrease in splice variant CD31 in the circulation, and not with the total level of circulating CD31.

The finding that CD31 is not lost on blood lymphocytes but only cleaved provides a unique opportunity to rescue its physiological immunoregulatory function by targeting the residual portion of the molecule. Specifically, the present invention provides peptides corresponding to juxta-membrane amino acids of the ectodomain of CD31 that are able to rescue the physiological immunoregulatory function of CD31, even in patients having apparently lost CD31 from the surface of their circulating T lymphocytes.

It has been demonstrated that such peptides are capable of preventing disease progression and aneurysm formation in a mouse model for atherosclerosis. Shorter and more stable peptides restricted to the last 10 or 6 COOH-terminal amino acids of the known peptide of twenty-three amino acids display superior in vitro immunosuppressive properties (lower ED and lower intra and inter-assay variability) than the known peptide. These amino acids correspond to a short extracellular fragment comprised between the membrane and the $6^{th}$ Ig-like domain of CD31.

The invention therefore provides peptides consisting of a fragment comprising the membrane juxta-proximal part of extracellular CD31 and part of the sixth Ig-like domain and the use of such peptides in the treatment of a thrombotic or an autoimmune as further described herein.

Such peptides have unique properties compared to soluble forms of CD31 comprising all or most Ig-like domains of CD31. Indeed, such peptides are highly homophilic since they have a Kd of $10^{-7}$ M, as assessed by BIAcore analysis. Hence they are able to engage CD31 signaling by bridging the membrane juxta-proximal part of extracellular CD31 that remains expressed after its cleavage, via a strong homo-oligomerization. In contrast to this, alternatively spliced soluble CD31 lacks the first 10 membrane juxta-proximal amino acids and shows weak homophilic binding with the 23-mer peptide (Kd of 17 µM, as assessed by BIAcore analysis). Furthermore, in vitro, only the peptides according to the invention are capable of engaging the ITIM pathway downstream of the truncated isoform of CD31, and are thus capable of restoring CD31 signaling in T lymphocytes having apparently lost CD31.

CD31 Peptides

It has been found that the six-amino-acid-long CD31 peptide of sequence SEQ ID NO: 2 and that a ten-amino-acid-long CD31 peptide of sequence SEQ ID NO: 3 are capable of inhibiting T-cell activation. These two peptides correspond to fragments comprising the membrane juxta-proximal part of extracellular CD31, which is adjacent to the sixth extracellular Ig-like domain of CD31.

Therefore, the invention is directed to an isolated peptide comprising or consisting of a fragment of CD31, wherein said fragment is selected from the group consisting of:
  a) a fragment of at least 3, 6 or 10 amino acids of the sequence defined by amino acids 579 to 601 of SEQ ID NO: 1;
  b) a fragment of at least 3, 6 or 10 amino acids of the sequence corresponding to (a) in a non-human mammalian CD31; or
  c) a sequence at least 80%, 85%, 90%, 95%, 96%, 97%, 98% or 99% identical to (a);
with the proviso that said peptide of (c) does not consist of an amino acid sequence of SEQ ID NO: 5 or 6.

As used herein, the term "peptide" has the meaning usually given in the art. More specifically, the dividing line between proteins and peptides is usually set at a length of approximately 50 amino acids. Thus the peptides according to the invention preferably have a length of at most 50, 40, 35, 30, 25, 20, 15 or 10 amino acids.

As used herein, the term "fragment" of a reference sequence refers to a chain of contiguous nucleotides or amino acids that is shorter than the reference sequence. More specifically, a fragment of the sequence defined by amino acids 579 to 601 of SEQ ID NO: 1 is at most 22 amino acids long. Said fragment may have a length of e.g. 3, 4, 5, 6, 7, 8, 9, 10, 11, 12, 13, 14, 15, 16, 17, 18, 19, 20, 21 or 22 amino acids. Preferably, said fragment has a length within the range of 3 to 18, 3 to 15, 3 to 10, 6 to 18, 6 to 15 or 6 to 10 amino acids.

The isolated peptide according to the invention may for example comprise or consist of a fragment having a sequence selected from the group consisting of SMRTSPRSSTLAVRVFLAPWKK (SEQ ID NO: 15, amino acids 2 to 23 of SEQ ID NO: 5), MRTSPRSSTLAVRVFLAPWKK (SEQ ID NO: 16, amino acids 3 to 23 of SEQ ID NO: 5), RTSPRSSTLAVRVFLAPWKK (SEQ ID NO: 17, amino acids 4 to 23 of SEQ ID NO: 5), TSPRSSTLAVRVFLAPWKK (SEQ ID NO: 18, amino acids 5 to 23 of SEQ ID NO: 5), SPRSSTLAVRVFLAPWKK (SEQ ID NO: 19, amino acids 6 to 23 of SEQ ID NO: 5), PRSSTLAVRVFLAPWKK (SEQ ID NO: 20, amino acids 7 to 23 of SEQ ID NO: 5), RSSTLAVRVFLAPWKK (SEQ ID NO: 21, amino acids 8 to 23 of SEQ ID NO: 5), SSTLAVRVFLAPWKK (SEQ ID NO: 22, amino acids 9 to 23 of SEQ ID NO: 5), STLAVRVFLAPWKK (SEQ ID NO: 23, amino acids 10 to 23 of SEQ ID NO: 5), TLAVRVFLAPWKK (SEQ ID NO: 24, amino acids 11 to 23 of SEQ ID NO: 5), LAVRVFLAPWKK (SEQ ID NO: 25, amino acids 12 to 23 of SEQ ID NO: 5), AVRVFLAPWKK (SEQ ID NO: 26, amino acids 13 to 23 of SEQ ID NO: 5), VRVFLAPWKK (SEQ ID NO: 3, amino acids 14 to 23 of SEQ ID NO: 5), RVFLAPWKK (SEQ ID NO: 27, amino acids 15 to 23 of SEQ ID NO: 5), VFLAPWKK (SEQ ID NO: 28, amino acids 16 to 23 of SEQ ID NO: 5), FLAPWKK (SEQ ID NO: 29, amino acids 17 to 23 of SEQ ID NO: 5), LAPWKK (SEQ ID NO: 2, amino acids 18 to 23 of SEQ ID NO: 5), APWKK (SEQ ID NO: 30, amino acids 19 to 23 of SEQ ID NO: 5), PWKK (SEQ ID NO: 31, amino acids 20 to 23 of SEQ ID NO: 5), WKK (amino acids 21 to 23 of SEQ ID NO: 5), HASSVPRSKILTVRVILAPWKK (SEQ ID NO: 32, amino acids 2 to 23 of SEQ ID NO: 6), ASVPRSKILTVRVILAPWKK (SEQ ID NO: 33, amino acids 3 to 23 of SEQ ID NO: 6), SSVPRSKILTVRVILAPWKK (SEQ ID NO: 34, amino acids 4 to 23 of SEQ ID NO: 6), SVPRSKILTVRVILAPWKK (SEQ ID NO: 35, amino acids 5 to 23 of SEQ ID NO: 6), VPRSKILTVRVILAPWKK (SEQ ID NO: 36, amino acids 6 to 23 of SEQ ID NO: 6), PRSKILTVRVILAPWKK (SEQ ID NO: 37, amino acids 7 to 23 of SEQ ID NO: 6), RSKILTVRVILAPWKK (SEQ ID NO: 38, amino acids 8 to 23 of SEQ ID NO: 6), SKILTVRVILAPWKK (SEQ ID NO: 39, amino acids 9 to 23 of SEQ ID NO: 6), KILTVRVILAPWKK (SEQ ID NO: 40, amino acids 10 to 23 of SEQ ID NO: 6), ILTVRVILAPWKK (SEQ ID NO: 41, amino acids 11 to 23 of SEQ ID NO: 6), LTVRVILAPWKK (SEQ ID NO: 42, amino acids 12 to 23 of SEQ ID NO: 6), TVRVILAPWKK (SEQ ID NO: 43, amino acids 13 to 23 of SEQ ID NO: 6), VRVILAPWKK (SEQ ID NO: 4, amino acids 14 to 23 of SEQ ID NO: 6), RVILAPWKK (SEQ ID NO: 44, amino acids 15 to 23 of SEQ ID NO: 6), VILAPWKK (SEQ ID NO: 45, amino acids 16 to 23 of SEQ ID NO: 6), ILAPWKK (SEQ ID NO: 46, amino acids 17 to 23 of SEQ ID NO: 6), SSMRTSPRSSTLAVRVFLAPWK (SEQ ID NO: 47, amino acids 1 to 22 of SEQ ID NO: 5), SSMRTSPRSSTLAVRVFLAPW (SEQ ID NO: 48, amino acids 1 to 21 of SEQ ID NO: 5), SSMRTSPRSSTLAVRVFLAP (SEQ ID NO: 49, amino acids 1 to 20 of SEQ ID NO: 5), SSMRTSPRSSTLAVRVFLA (SEQ ID NO: 50, amino acids 1 to 19 of SEQ ID NO: 5), SSMRTSPRSSTLAVRVFL (SEQ ID NO: 51, amino acids 1 to 18 of SEQ ID NO: 5), SSMRTSPRSSTLAVRVF (SEQ ID NO: 52, amino acids 1 to 17 of SEQ ID NO: 5), SSMRTSPRSSTLAVRV (SEQ ID NO: 5, amino acids 1 to 16 of SEQ ID NO: 5), SSMRTSPRSSTLAVR (SEQ ID NO: 53, amino acids 1 to 15 of SEQ ID NO: 5), SSMRTSPRSSTLAV (SEQ ID NO: 54, amino acids 1 to 14 of SEQ ID NO: 5), SSMRTSPRSSTLA (SEQ ID NO: 55, amino acids 1 to 13 of SEQ ID NO: 5), SSMRTSPRSSTL (SEQ ID NO: 56, amino acids 1 to 12 of SEQ ID NO: 5), SSMRTSPRSST (SEQ ID NO: 57, amino acids 1 to 11 of SEQ ID NO: 5), SSMRTSPRSS (SEQ ID NO: 58, amino acids 1 to 10 of SEQ ID NO: 5), SSMRTSPRS (SEQ ID NO: 59, amino acids 1 to 9 of SEQ ID NO: 5), SSMRTSPR (SEQ ID NO: 60, amino acids 1 to 8 of SEQ ID NO: 5), SSMRTSP (SEQ ID NO: 61, amino acids 1 to 7 of SEQ ID NO: 5), SSMRTS (SEQ ID NO: 62, amino acids 1 to 6 of SEQ ID NO: 5), SSMRT (SEQ ID NO: 63, amino acids 1 to 5 of SEQ ID NO: 5), SSMR (SEQ ID NO: 64, amino acids 1 to 4 of SEQ ID NO: 5), SSM (amino acids 1 to 3 of SEQ ID NO: 5), NHASSVPRSKILTVRVILAPWK (SEQ ID NO: 65, amino acids 1 to 22 of SEQ ID NO: 6), NHASSVPRSKILTVRVILAPW (SEQ ID NO: 66, amino acids 1 to 21 of SEQ ID NO: 6), NHASSVPRSKILTVRVILAP (SEQ ID NO: 67, amino acids 1 to 20 of SEQ ID NO: 6), NHASSVPRSKILTVRVILA (SEQ ID NO: 68, amino acids 1 to 19 of SEQ ID NO: 6), NHASSVPRSKILTVRVIL (SEQ ID NO: 69, amino acids 1 to 18 of SEQ ID NO: 6), NHASSVPRSKILTVRVI (SEQ ID NO: 70, amino acids 1 to 17 of SEQ ID NO: 6), NHASSVPRSKILTVRV (SEQ ID NO: 71, amino acids 1 to 16 of SEQ ID NO: 6), NHASSVPRSKILTVR (SEQ ID NO: 72, amino acids 1 to 15 of SEQ ID NO: 6), NHASSVPRSKILTV (SEQ ID NO: 73, amino acids 1 to 14 of SEQ ID NO: 6), NHASSVPRSKILT (SEQ ID NO: 74, amino acids 1 to 13 of SEQ ID NO: 6), NHASSVPRSKIL (SEQ ID NO: 75, amino acids 1 to 12 of SEQ ID NO: 6), NHASSVPRSKI (SEQ ID NO: 76, amino acids 1 to 11 of SEQ ID NO: 6), NHASSVPRSK (SEQ ID NO: 77, amino acids 1 to 10 of SEQ ID NO: 6), NHASSVPRS (SEQ ID NO: 78, amino acids 1 to 9 of SEQ ID NO: 6), NHASSVPR (SEQ ID NO: 79, amino acids 1 to 8 of SEQ ID NO: 6), NHASSVP (SEQ ID NO: 80, amino acids 1 to 7 of SEQ ID NO: 6), NHASSV (SEQ ID NO: 81, amino acids 1 to 6 of SEQ ID NO: 6), NHASS (SEQ ID NO: 82, amino acids 1 to 5 of SEQ ID NO: 6), NHAS (SEQ ID NO: 83, amino acids 1 to 4 of SEQ ID NO: 6), NHA (amino acids 1 to 3 of SEQ ID NO: 6), SMRTSPRSSTLAVRVFLAPWK (SEQ ID NO: 84, amino acids 2 to 22 of SEQ ID NO: 5), MRTSPRSSTLAVRVFLAPW (SEQ ID NO: 85, amino acids 3 to 21 of SEQ ID NO: 5), RTSPRSSTLAVRVFLAP (SEQ ID NO: 86, amino acids 4 to 20 of SEQ ID NO: 5), TSPRSSTLAVRVFLA (SEQ ID NO: 87, amino acids 5 to 19 of SEQ ID NO: 5), SPRSSTLAVRVFL (SEQ ID NO: 88, amino acids 6 to 18 of SEQ ID NO: 5), PRSSTLAVRVF (SEQ ID NO: 89, amino acids 7 to 17 of SEQ ID NO: 5), RSSTLAVRV (SEQ ID NO: 90, amino acids 8 to 16 of SEQ ID NO: 5), SSTLAVR (SEQ ID NO: 91, amino acids 9 to 15 of SEQ ID NO: 5), STLAV (SEQ ID NO: 92, amino acids 10 to 14 of SEQ ID NO: 5), TLA (amino acids 11 to 13 of SEQ ID NO: 5), HASSVPRSKILTVRVILAPWK (SEQ ID NO: 93, amino acids 2 to 22 of SEQ ID NO: 6), ASSVPRSKILTVRVILAPW (SEQ ID NO: 94, amino acids 3 to 21 of SEQ ID NO: 6), SSVPRSKILTVRVILAP (SEQ ID NO: 95, amino acids 4 to 20 of SEQ ID NO: 6), SVPRSKILTVRVILA (SEQ ID NO: 96, amino acids 5 to 19 of SEQ ID NO: 6), VPRSKILTVRVIL (SEQ ID NO: 97, amino acids 6 to 18 of SEQ ID NO: 6), PRSKILTVRVI (SEQ ID NO: 98, amino acids 7 to 17 of SEQ ID NO: 6), RSKILTVRV (SEQ ID NO: 99, amino acids 8 to 16 of SEQ ID NO: 6), SKILTVR (SEQ ID NO: 100, amino acids 9 to 15 of SEQ ID NO: 6), KILTV (SEQ ID NO: 101, amino acids 10 to 14 of SEQ ID NO: 6) and ILT (amino acids 11 to 13 of SEQ ID NO: 6).

In a preferred embodiment, said fragment corresponds to a juxta-membrane fragment, i.e. to a fragment immediately adjacent to the transmembrane domain of CD31. In other words, said fragment preferably corresponds to a fragment including the C-terminal extremity of the sequence consisting of amino acids 579 to 601 of SEQ ID NO: 1 or of the corresponding sequence in a non-human mammalian CD31. For example, a peptide consisting of a juxta-membrane fragment of 15 amino acids of the sequence defined by amino acids 579 to 601 of SEQ ID NO: 1 consists of amino acids 587 to 601 of SEQ ID NO: 1.

In a specific embodiment, peptides comprising the transmembrane domain of CD31 or part thereof are excluded from the scope of the present invention.

The sequence of CD31 peptides according to the invention is preferably derived from the sequence of human or murine CD31. However, the sequence of CD31 may be derived from any non-human mammalian CD31 sequence. FIG. 1 shows an alignment between the human, murine, bovine and pig CD31 sequences. The sequence corresponding to the sequence defined by amino acids 579 to 601 of SEQ ID NO: 1 is highlighted by a box. The skilled in the art can easily identify the corresponding sequence in another non-human mammalian CD31 protein by performing a sequence alignment with the sequences shown in FIG. 1.

In addition to the CD31 fragment, the peptide may optionally comprise sequences heterologous to CD31. These heterologous sequences may e.g. correspond to a carrier molecule such as the Keyhole Limpet Hemocyanin (KLH), bovine serum albumin (BSA), ovalbumin (OVA), thyroglobulin (THY) or the multiple antigenic peptide (MAP).

In a preferred embodiment, the peptide comprises or consists of a peptide selected from the group consisting of:
the six-amino-acid-long peptide shown as SEQ ID NO: 2, which is present both in human and murine CD31 sequences;
the ten-amino-acid-long peptide shown as SEQ ID NO: 3, the sequence of which is derived from the mouse CD31 sequence; and
the ten-amino-acid-long peptide shown as SEQ ID NO: 4, the sequence of which is derived from the human CD31 sequence.

In another preferred embodiment, the peptide comprises or consists of an amino acid sequence at least 80%, 85%, 90%, 95%, 96%, 97%, 98% or 99% identical to any one of SEQ ID NOs: 2, 3 or 4.

CD31 peptides according to the invention have the biological activity of exerting a dose-dependent inhibition of T-cell proliferation in vitro and/or of inhibiting the mixed-lymphocyte reaction (MLR). Their biological activity may for example be measured as described in Example 3, Example 6 or in Zehnder et al. (1995, Blood. 85(5):1282-8).

The T-cell proliferation assay may comprise comparing the radioactivity incorporated into T-cells cultured either in the presence or in the absence of the compound to be tested. This assay may for example be performed as follows:
providing a multi-well plate comprising complete medium supplemented with anti-CD3 antibodies;
supplementing the wells with increasing concentrations of the compound to be tested;
plating peripheral blood mononuclear cells (e.g. of spleen cells);
culturing the cells for about 72 hours;
adding ($^3$H) thymidine and culturing the cells for about 16 hours;
measuring the radioactivity; and
comparing the radioactivity measured in the presence of the compound to be tested with the radioactivity measured in the absence of said compound, and/or in the presence of a reference compound, and/or in the presence of a negative control.

Alternatively, the T-cell proliferation assay may comprise comparing expression levels of the early activation marker CD69 in T-cells cultured either in the presence or in the absence of the compound to be tested. This assay may for example be performed as follows:
providing purified CD4+ cells (e.g. purified from C57B16 mice);
stimulating said CD4+ cells by addition of anti-CD3 purified antibodies and bone marrow derived dendritic cells;
culturing the cells for about 18 hours; and
analyzing said cells for the expression of the early activation marker CD69, e.g. by flow cytometry; and
comparing CD69 expression in the presence of the compound to be tested.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

Methods for comparing the identity and homology of two or more sequences are well known in the art. Thus for instance, programs available in the Wisconsin Sequence Analysis Package, version 9.1, for example the programs BESTFIT and GAP, may be used to determine the % identity between two polynucleotides and the % identity and the % homology between two polypeptide sequences. BESTFIT uses the "local homology" algorithm of Smith and Waterman and finds the best single region of similarity between two sequences. Other programs for determining identity and/or similarity between sequences are also known in the art, for instance the BLAST family of programs, accessible through the home page of the NCBI at world wide web site ncbi.nlm.nih.gov) and FASTA.

Peptides consisting of an amino acid sequence "at least 80%, 85%, 90%, 95%, 96%, 97%, 98% or 99% identical" to a reference sequence may comprise mutations such as deletions, insertions and/or substitutions compared to the reference sequence. In case of substitutions, the substitution preferably corresponds to a conservative substitution as indicated in the table below. In a preferred embodiment, the peptide consisting of an amino acid sequence at least 80%, 85%, 90%, 95%, 96%, 97%, 98% or 99% identical to a reference sequence only differs from the reference sequence by conservative substitutions. In another preferred embodiment, the peptide consisting of an amino acid sequence at least 80%, 85%, 90%, 95%, 96%, 97%, 98% or 99% identical to a reference sequence corresponds to a naturally-occurring allelic variant of the reference sequence. In still another preferred embodiment, the peptide consisting of an amino acid sequence at least 80%, 85%, 90%, 95%, 96%, 97%, 98% or 99% identical to a reference sequence corresponds to a homologous sequence derived from another non-human mammalian species than the reference sequence.

| Conservative substitutions | Type of Amino Acid |
| --- | --- |
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

In a preferred embodiment, the peptide according to the invention consists of any one of the sequences shown in the table below:

| species | Swissprot accession number | position | sequence | SEQ ID NO: |
| --- | --- | --- | --- | --- |
| Human | P16284 | 592-601 | VRVILAPWKK | 4 |
| Mouse | Q08481 | 581-590 | VRVFLAPWKK | 3 |
| Rat | Q3SWT0 | 580-589 | VRVFLAPWKK | 10 |
| Pig | Q95242 | 593-602 | VRVYLAPWKK | 11 |
| Bovin | P51866 | 591-600 | VRVYL-PLEK | 12 |

CD31 peptides according to the invention may be prepared by any well-known procedure in the art, such as solid phase synthesis, liquid phase synthesis or genetic engineering. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. After synthesis of the desired peptide, it is subjected to the deprotection reaction and cut out from the solid support.

The CD31 peptides of the invention may optionally comprise chemical modifications improving their stability and/or their bioavailability. Such chemical modifications aim at obtaining peptides with increased protection of the peptides against enzymatic degradation in vivo, and/or increased capacity to cross membrane barriers, thus increasing its half-life and maintaining or improving its biological activity. Any chemical modification known in the art can be employed according to the present invention. Such chemical modifications include but are not limited to:

- modifications to the N-terminal and/or C-terminal ends of the peptides such as e.g. N-terminal acylation (preferably acetylation) or desamination, or modification of the C-terminal carboxyl group into an amide or an alcohol group;
- modifications at the amide bond between two amino acids: acylation (preferably acetylation) or alkylation (preferably methylation) at the nitrogen atom or the alpha carbon of the amide bond linking two amino acids;
- modifications at the alpha carbon of the amide bond linking two amino acids such as e.g. acylation (preferably acetylation) or alkylation (preferably methylation) at the alpha carbon of the amide bond linking two amino acids;
- chirality changes such as e.g. replacement of one or more naturally occurring amino acids (L enantiomer) with the corresponding D-enantiomers;
- retro-inversions in which one or more naturally-occurring amino acids (L-enantiomer) are replaced with the corresponding D-enantiomers, together with an inversion of the amino acid chain (from the C-terminal end to the N-terminal end);
- azapeptides, in which one or more alpha carbons are replaced with nitrogen atoms; and/or
- betapeptides, in which the amino group of one or more amino acid is bonded to the β carbon rather than the α carbon.

By an "isolated" peptide, it is intended that the peptide is not present within a living organism, e.g. within human body. However, the isolated peptide may be part of a composition or a kit. The isolated peptide is preferably purified.

The compounds of the invention may be produced by any well-known procedure in the art, including chemical synthesis technologies and recombinant technologies.

Examples of chemical synthesis technologies are solid phase synthesis and liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoe (t-butoxycarbonyl), Cl—Z (2-chlorobenzyloxycarbonyl), Br—Z (2-bromobenzyloyycarbonyl), Bzl (benzyl), Fmoc (9-fluorenylmcthoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Clz-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method.

Alternatively, the peptide may be synthesized using recombinant techniques. In this case, a nucleic acid encoding a peptide according to the invention (further referred to as "a nucleic acid according to the invention") is cloned into an expression vector. The nucleic acid of the invention is preferably placed under the control of expression signals (e.g. a promoter, a terminator and/or an enhancer) allowing its expression. The expression vector is then transfected into a host cell (e.g. a human, CHO, mouse, monkey, fungal or bacterial host cell), and the transfected host cell is cultivated under conditions suitable for the expression of the peptide.

The method of producing the peptide may optionally comprise the steps of purifying said peptide, chemically modifying said peptide, and/or formulating said peptide into a pharmaceutical composition.

The invention also encompasses a method for identifying a peptidomimetic of a peptide according to the invention, said peptidomimetic being a candidate compound for the treatment and/or prevention of a thrombotic or an autoimmune disorder, comprising the steps of:
 a) providing a peptidomimetic; and
 b) determining whether said peptidomimetic exerts:
  i. a dose-dependent inhibition of T-cell proliferation in vitro and/or of the mixed-lymphocyte reaction (MLR);
  ii. an immunosuppressant activity; and/or
  iii. an antiplatelet activity.
wherein, if said peptidomimetic exerts a dose-dependent inhibition of T-cell proliferation in vitro and/or of the mixed-lymphocyte reaction (MLR), an immunosuppressant activity and/or an antiplatelet activity, said peptidomimetic is a candidate compound for the treatment and/or prevention of a thrombotic or an autoimmune disorder.

Step (a) of the above method may comprise designing and synthesizing said peptidomimetic.

Step (b) of the above method for identifying a peptidomimetic of a peptide according to the invention may comprise or consist of (i); (ii); (iii); (i) and (ii); (i) and (iii); (ii) and (iii); or (i) and (ii) and (iii).

Methods for determining whether said peptidomimetic exerts a dose-dependent inhibition of T-cell proliferation in vitro and/or of the mixed-lymphocyte reaction (MLR), an immunosuppressant activity and/or an antiplatelet activity are well known to the skilled in the art.

The determination whether said peptidomimetic exerts a dose-dependent inhibition of T-cell proliferation in vitro and/or of the mixed-lymphocyte reaction (MLR) may for example be performed as described in Example 3.

Immunosuppressant and antiplatelet activity can for example be the evaluated by analyzing the expression of activation surface markers (e.g. CD62P for platelets and/or CD69 for leukocytes) or of soluble activation markers (e.g. TXA2 for platelets and/or IL-2 for Lymphocytes).

As used herein, the term <<peptidomimetic>> refers to a compound containing non-peptidic structural elements that mimics the biological action of a CD31 peptide according to the invention. Methods for designing and synthesizing peptidomimetics of a given peptide are well-known in the art and include e.g. those described in Ripka and Rich (Curr Opin Chem Biol. 1998; 2(4):441-52) and in Patch and Barron (Curr Opin Chem Biol. 2002; 6(6):872-7).

Use of CD31 Peptides for the Treatment of Thrombotic and Autoimmune Disorders

It has been found that CD31 peptides corresponding to fragments comprising part of the sixth extracellular Ig-like domain of CD31 are capable of activating CD31-mediated signaling, even in CD31$^-$ (i.e. CD31$^{shed}$) T lymphocytes. In addition, such peptides are capable of preventing disease progression and aneurysm formation in a mouse model for atherosclerosis.

Therefore, the invention is directed to an isolated peptide comprising or consisting of
  a) amino acids 579 to 601 of SEQ ID NO: 1;
  b) the amino acids corresponding to (a) in a non-human mammalian CD31;
  c) a fragment of at least 6 amino acids of (a);
  d) a fragment of at least 6 amino acids of (b); or
  e) a sequence at least 80% identical to (a) or (c);
for use in activating CD31-mediated signaling. These peptides preferably exert a dose-dependent inhibition of T-cell proliferation in vitro. The activation of CD31-mediated signaling may be an in vitro or an in vivo activation.

As used throughout the present specification, the term "CD31-mediated signaling" refers to a signaling pathway in which CD31 is involved. Such pathways are well known in the art and include those described e.g. in Newman and Newman (2003 Arterioscler Thromb Vasc Biol 23:953-964) and in Newton-Nash and Newman (1999. J Immunol 163: 682-688).

The invention is further directed to an isolated peptide comprising or consisting of:
  a) amino acids 579 to 601 of SEQ ID NO: 1;
  b) the amino acids corresponding to (a) in a non-human mammalian CD31;
  c) a fragment of at least 6 amino acids of (a);
  d) a fragment of at least 6 amino acids of (b); or
  e) a sequence at least 80% identical to (a) or (c);
for use in the treatment of a thrombotic or an autoimmune disorder. These peptides preferably exert a dose-dependent inhibition of T-cell proliferation in vitro.

As used throughout the present specification, the term "autoimmune disorder" includes but is not limited to rheumatoid arthritis (RA), multiple sclerosis (MS), inflammatory bowel disease (IBD), systemic lupus erythematosus (SLE), Graves' disease and diabetes mellitus.

As used throughout the present specification, the term "autoimmune disorder" includes but is not limited to rheumatoid arthritis (RA), multiple sclerosis (MS), inflammatory bowel disease (IBD), systemic lupus erythematodes (SLE), Graves' disease and diabetes mellitus.

In a preferred embodiment of the invention, said thrombotic or autoimmune disorder is associated with a loss of CD31$^+$ T lymphocytes phenotype. Indeed, it has been surprisingly found that CD31 peptides restore CD31 signaling even in individuals with a CD31$^-$ T lymphocytes phenotype. Therefore, in the context of the present invention, CD31 peptides are preferably used to treat a subgroup of individuals and/or patients having a CD31$^-$ T lymphocytes phenotype.

As used herein, the term "CD31$^-$ T lymphocytes phenotype" is used interchangeably with the term "CD31$^{shed}$ T lymphocytes phenotype". These terms refer to the phenotype of an individual having apparently lost CD31 on its circulating T cells when conventional prior art methods for detecting CD31, e.g. such as those described in Stockinger et al. (Immunology, 1992, 75(1):53-8), Demeure et al. (Immunology, 1996, 88(1):110-5), Caligiuri et al. (Arterioscler Thromb Vasc Biol, 2005, 25(8):1659-64) or Caligiuri et al. (Arterioscler Thromb Vasc Biol, 2006, 26(3):618-23) are used. In such methods, the antibody used for detecting CD31 binds to an epitope located on any one of the 1$^{st}$ to the 5$^{th}$ extracellular Ig-like domains.

Preferably, individuals having a CD31$^-$ T lymphocytes phenotype have lost at least 50%, 60%, 65%, 70%, 75%, 80%, 90% or 95% of their circulating CD4$^+$/CD31$^+$ T lymphocytes. In other words, at least 50%, 60%, 65%, 70%, 75%, 80%, 90% or 95% of their circulating T lymphocytes are CD31$^{shed}$ lymphocytes. Either the plasmatic rate or the cellular rate of CD31$^-$ T lymphocytes, compared to CD31$^+$ T lymphocytes, may be measured.

The CD31 peptide used for activating CD31-mediated signaling and/or treating a thrombotic or an autoimmune disorder may be any one of the peptides described in the above paragraph entitled "CD31 peptides".

Alternatively, the CD31 peptide used for activating CD31-mediated signaling and/or treating a thrombotic or an autoimmune disorder comprises or consists of:
  a) amino acids 579 to 601 of SEQ ID NO: 1;
  b) the amino acids corresponding to (a) in a non-human mammalian CD31;
  c) a sequence at least 80%, 85%, 90%, 95%, 96%, 97%, 98% or 99% identical to (a) or (b);

The peptides used herein may have a length comprised between e.g. 10-100, 15-80, 20-60, 25-50 and 20-40 amino acids. These peptides preferably comprise or consist of fragments immediately adjacent to the transmembrane domain of CD31. The peptide may for example correspond to a peptide consisting of an amino acid sequence at least 80%, 85%, 90%, 95%, 96%, 97%, 98% or 99% identical to SEQ ID NO: 5 or 6. The peptide preferably consists of SEQ ID NO: 5 or 6. These peptides may optionally comprise chemical modifications improving their stability and/or their bioavailability.

The invention is also directed to a method of treating or preventing a thrombotic or an autoimmune disorder comprising the step of administering an effective amount of a peptide as described herein, or a nucleic coding therefore, to an individual in need thereof. Said individual in need thereof preferably suffers from or is at risk of suffering from a thrombotic or an autoimmune disorder. Most preferably, said individual has a CD31$^-$ T lymphocytes phenotype.

By "effective amount", is meant an amount sufficient to achieve a concentration of peptide which is capable of preventing, treating or slowing down the disease to be treated. Such concentrations can be routinely determined by those of skilled in the art. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like. It will also be appreciated by those of stalled in the art that the dosage may be dependent on the stability of the administered peptide.

The individuals to be treated in the frame of the invention are preferably human individuals. However, the veterinary use of CD31 peptides for treating other mammals is also contemplated by the present invention.

Pharmaceutical Compositions

The CD31 peptides described herein may be formulated into a pharmaceutical composition. Thus the invention contemplates a pharmaceutical composition comprising any one of the above CD31 peptides and a physiologically acceptable carrier. Physiologically acceptable carriers can be prepared by any method known by those skilled in the art.

Pharmaceutical compositions comprising at least one peptide of the invention include all compositions wherein the peptide(s) are contained in an amount effective to achieve the intended purpose. In addition, the pharmaceutical compositions may contain suitable pharmaceutically acceptable carriers comprising excipients and auxiliaries which facilitate processing of the active compounds into preparations which can be used pharmaceutically. Suitable pharmaceutically acceptable vehicles are well known in the art and are described for example in Remington's Pharmaceutical Sciences (Mack Publishing Company, Easton, USA, 1985), which is a standard reference text in this field. Pharmaceutically acceptable vehicles can be routinely selected in accordance with the mode of administration, solubility and stability of the peptides. For example, formulations for intravenous administration may include sterile aqueous solutions which may also contain buffers, diluents and other suitable additives. The use of biomaterials and other polymers for drug delivery, as well the different techniques and models to validate a specific mode of administration, are disclosed in literature.

The peptides of the present invention may be administered by any means that achieve the intended purpose. For example, administration may be achieved by a number of different routes including, but not limited to subcutaneous, intravenous, intradermal, intramuscular, intraperitoneal, intracerebral, intrathecal, intranasal, oral, rectal, transdermal, buccal, topical, local, inhalant or subcutaneous use.

Dosages to be administered depend on individual needs, on the desired effect and the chosen route of administration. It is understood that the dosage administered will be dependent upon the age, sex, health, and weight of the recipient, concurrent treatment, if any, frequency of treatment, and the nature of the effect desired. The total dose required for each treatment may be administered by multiple doses or in a single dose.

Depending on the intended route of delivery, the compounds may be formulated as liquid (e.g., solutions, suspensions), solid (e.g., pills, tablets, suppositories) or semisolid (e.g., creams, gels) forms.

In a preferred embodiment, the compositions are presented in unit dosage forms to facilitate accurate dosing. The term "unit dosage forms" refers to physically discrete units suitable as unitary dosages for human subjects and other mammals, each unit containing a pre-determined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form.

The compounds of this invention can also be administered in sustained release forms or from sustained release drug delivery systems.

The expression "physiologically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution.

Besides the pharmaceutically acceptable carrier, the compositions of the invention can also comprise minor amounts of additives, such as stabilizers, excipients, buffers and preservatives.

The invention also contemplates a pharmaceutical composition comprising a nucleic acid encoding the peptide of the invention in the frame of e.g. a treatment by gene therapy. In this case, the nucleic acid is preferably present on a vector, on which the sequence coding for the peptide is placed under the control of expression signals (e.g. a promoter, a terminator and/or an enhancer) allowing its expression. The vector may for example correspond to a viral vector such as an adenoviral or a lentiviral vector.

The invention further provides kits comprising a pharmaceutical composition comprising a CD31 peptide of the invention and instructions regarding the mode of administration. These instructions may e.g. indicate the medical indication, and/or the route of administration, and/or the dosage, and/or the group of patients to be treated.

All references cited herein, including journal articles or abstracts, published or unpublished patent application, issued patents or any other references, are entirely incorporated by reference herein, including all data, tables, figures and text presented in the cited references.

Although having distinct meanings, the terms "comprising", "having", "containing' and "consisting of" have been used interchangeably throughout this specification and may be replaced with one another.

The invention will be further evaluated in view of the following examples and figures.

BRIEF DESCRIPTION OF THE FIGURES

FIG. 1A-B shows an alignment between the sequences of human, mouse, pig and bovine CD31. The sequence defined by amino acids 579 to 601 of SEQ ID NO: 4 (human CD31) and the corresponding sequence in mouse, pig and bovine CD31 is highlighted by a box.

FIG. 5A-D shows that CD31 homotypic peptide 551-574 inhibits T-cell responses. a. BIAcore® analysis of mouse CD31 peptide 551-574 homophilic binding at two-fold stepwise dilutions of the analyte (12.5, 25, 50 and 100 µM). Data are normalised against the control channels and expressed as ΔRU (Resonance Units). b. TCR-induced intracellular calcium mobilisation determined by flow cytometry in Fluo-3AM-loaded spleen cells. Data are expressed as MFI (530/30 nm). Grey arrow=addition of either anti-CD3/CD28 antibodies and crosslinker alone (■=control) or with peptide 551-554 at 100 µM (●) or with anti-mouse CD31 antibodies (○). c. Proliferation in response to TCR-stimulation in CD31+/+ (black columns) and CD31−/− (white columns) spleen cells. A dose-dependent inhibition is observed in CD31+/+ cells while only the highest dose of the peptide affect proliferation of CD31−/− splenocytes. No effect was observed with 100 µM dose of the scramble peptide on CD31+/+ cells (crisscross column). *p<0.05 vs previous peptide dose. d. Immunosuppressive effect of the peptide in the DTH model. *p<0.01 vs scramble (crisscross column) and 10 µM dose of peptide 551-574. Data are expressed as mean±SEM.

BRIEF DESCRIPTION OF THE SEQUENCES

Figure 2:
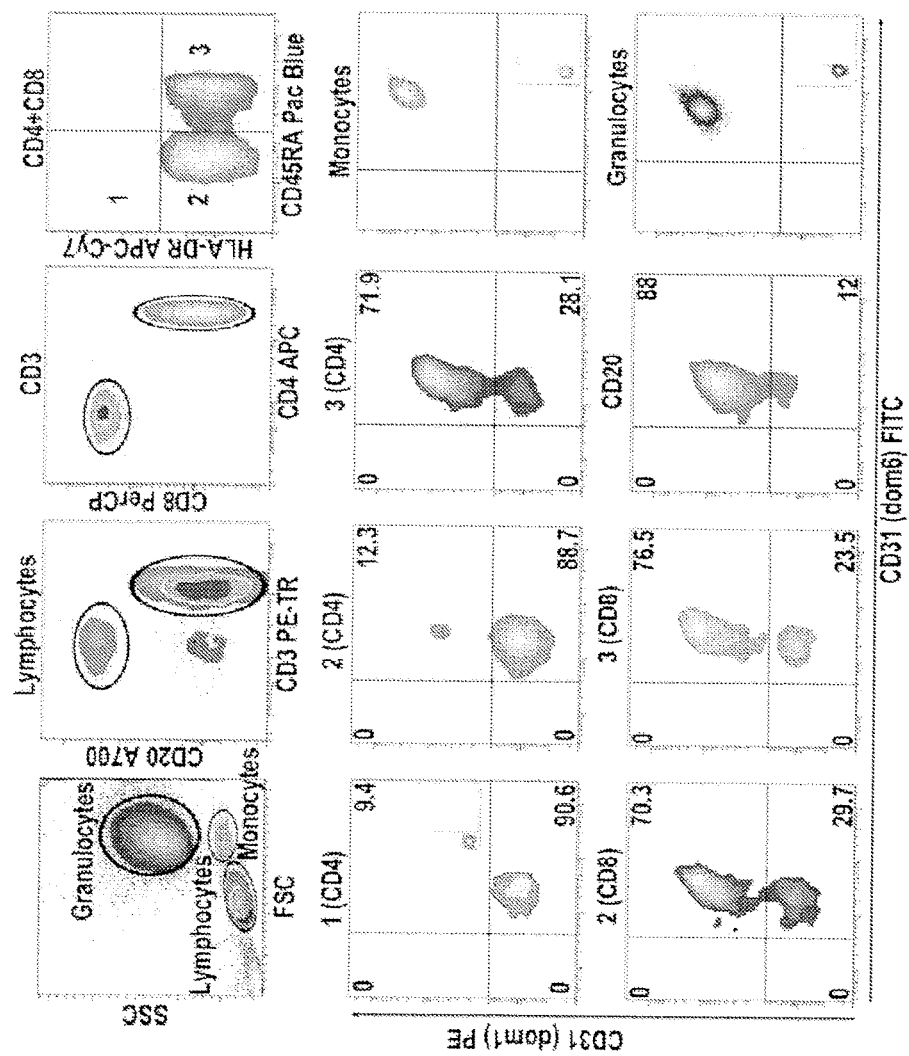
FIG. 2 shows a representative example of 10-color flow-cytometry analysis of human peripheral blood cells from a healthy donor. Isotype controls of antibodies anti-CD31 dom1 and anti-CD31 dom6 are shown in the insets. Lymphocytes, Monocytes and Granulocytes were gated within the FSC/SSC scatter. B (CD20 A700+) and T (CD3 PE-TR+) lymphocytes were identified and gated within the "Lymphocytes" and CD8+ (PerCP) and CD4+ (APC) subpopulations were gated within T lymphocytes. CD8+ and CD4+ T cells were further analyzed for the expression of HLA-DR and CD45RA and accordingly subdivided in activated (1), memory (2) and naïve (3) cells. All leukocytes were positive for CD31 dom6. Lack of dom1 increased from naïve (3) to memory (2) to activated (1) T cells.

SEQ ID NO: 1 corresponds to the sequence of human CD31.

SEQ ID NOs: 2, 3, 4, 10, 11 and 12 correspond to CD31 peptides according to the invention.

SEQ ID NOs: 5 and 6 correspond to CD31 peptides for use in the methods according to the invention.

SEQ ID NO: 7 corresponds to the sequence of murine CD31.

SEQ ID NO: 8 corresponds to the sequence of bovine CD31.

SEQ ID NO: 9 corresponds to the sequence of pig CD31.

SEQ ID NOs: 13 and 14 correspond to scramble peptides used as controls.

SEQ ID Nos: 15 to 101 correspond to CD31 peptides according to the invention.

EXAMPLES

Example 1: Material and Methods

Assessment of CD31$^+$ and CD31$^{shed}$ blood leukocytes. Ten-color flow cytometry was performed on peripheral blood leukocytes from 5 healthy individuals either in basal conditions or after overnight stimulation with soluble 1 µg/ml of purified anti-CD3 antibody (R&D Systems). Ten-color flow cytometry was performed after erythrocyte hypotonic lysis (10 minutes at 37° C. 1:10 v:v in Tris 10 mM, NH$_4$Cl 155 mM, KHCO$_3$ 10 mM, pH 7.4) on heparinized peripheral blood leukocytes from 5 healthy individuals, fixed in PBS/Formaldehyde 1%/FCS 1% for 4 minutes at 37° C. prior to processing. All experiments on human blood were approved by the International Ethical committee (see world wide web page clinicaltrials.gov; Identifier: NCT00430820). Pelleted cells were incubated for 30 minutes at room temperature and protected from light with a cocktail of fluorescent monoclonal antibodies directed to CD3, CD4, CD8, HLA-DR, CD45RA, and CD31 (WM59) from BD Biosciences and anti-CD20 and anti-CD31 (PE-CAM 1.2) from Invitrogen (1 µl of each). At least 50,000 events were acquired in the lymphocyte gate using a BD LSRII® equipped with 3 lasers (405, 488 and 633 nm) and analysed with BD DIVA® 6.0 software.

Subtractive Measurement of Soluble CD31.

To detect the splice variant and truncated CD31 in plasma and the culture supernatant, a cytokine bead array (CBA®, BD) has been customized. Three differently functional CBA beads (A9, D5 and E9) were coupled with either one of the following purified monoclonal anti-CD31 antibodies JC70A (domain 1, DAKO), MEM-05 (domain 5, Zymed) and PECAM 1.2 (domain 6, Invitrogen). The coupled beads were then incubated with the plasma of the same 5 healthy controls (FIG. 2) or the culture supernatant and positive binding of circulating CD31 was detected by a fourth anti-CD31 monoclonal antibody, WM-59 (domains 1-2)

coupled to PE (BD). The concentration of plasma CD31 including at least domain 1 (JC70A), or domains 1 to 5 (MEM-05) or all the extracellular domains 1 to 6 of CD31 (PECAM 1.2) was determined by analysing the median fluorescent intensity of the detecting antibody on ≥1000 gated beads on samples and serial dilutions of the same standard (recombinant, full length extracellular CD31, R&D Systems). The standard curve was obtained for each of the beads using the same known concentrations of the recombinant CD31 in order to overcome any bias due to differences in binding affinity of the diverse antibodies. The concentration in ng/ml of CD31 determined with PECAM 1.2 coupled beads (dom 1-6) was subtracted from the one obtained using MEM-05 coupled beads to obtain the amount of circulating CD31 lacking dom6 (dom 1-5). The latter was subtracted from the concentration of CD31 obtained using the JC70A-coupled beads to calculate the value of soluble CD31 lacking both dom 5 and 6 but containing at least domains 1 and 2 (dom 1-2).

Assessment of CD31-ITIM Phosphorylation.

Log-phase Jurkat cells ($10^7$ cells/condition) were either left unstimulated (negative control) or incubated with pervanadate (positive control) or stimulated with anti-CD3 and anti-CD28 antibodies (R&D Systems, 1 µg/ml each) in the presence or absence of peptide 551-574 (100 µM), or incubated with the peptide alone during 20 minutes. Cells were then lysed with 1 ml of RIPA buffer on ice for 30 minutes, ultracentrifuged and 16 µl of the supernatant was incubated with PECAM 1.2-coated Functional E9 CBA® beads (BD) for 2 hours at room temperature. Beads were subsequently washed with CBA washing buffer and incubated with 2 µl of undiluted rabbit anti-CD31 phosphotyrosine 686 (pY686) sera followed by two washings and incubation with AlexaFluor®488-conjugated (Fab')$_2$ fragments (1:100 in CBA whashing buffer) of goat-anti-rabbit IgG (Invitrogen). The beads (2000/condition) were finally analysed by flow cytometry in the FITC channel (530/30 nm) and data are expressed as Median fluorescence intensity (MFI)±the percentage of the coefficient of variability (% CV) calculated with the DIVA 6.0® software (BD). Duplicate lysate aliquots and serial dilutions of recombinant CD31 were incubated with the PECAM 1.2-coated beads and the amount of dom1+ cell-bound CD31 was revealed using anti-CD31 WM59-R-PE (dom1) and PECAM 1.2-FITC (dom6) antibodies (data shown in FIG. 3a).

Fluorescent Peptide Binding.

For visualisation of peptide binding to $CD31^+$ and $CD31^{shed}$ $CD4^+$ T cells, freshly purified peripheral blood leukocytes prepared as above were washed with a buffered solution containing 2 mM EDTA (to avoid endocytosis of the peptide) and incubated overnight at room temperature in a dark humidified chamber with 50 µM FITC-labelled CD31 peptide 551-574 and 1:10 dilution of fluorescent monoclonal anti-CD31 (PE) and anti-CD4 (APC) antibodies (BD Biosciences) in a poly-D-Lysine coated Ibidi® 8-well culture chamber (Biovalley). Cells were then washed twice, nuclei counterstained with DAPI and digital images of a 0.3 µm intracellular section were acquired on a Zeiss Axiovert M200 microscope (x63 immersion objective) equipped with the ApoTome® and a cooled monochromatic digital camera (Zeiss).

Calcium Mobilisation Assay.

Spleen cells from C57Bl/6 mice were prepared as described in Caligiuri et al. (2005 Arterioscler Thromb Vasc Biol 25:1659-1664). Cells were incubated with Fluo-3AM (Invitrogen, # F1242) as per the instructions of the manufacturer. Fluorescence of calcium-bound tracer was measured in the FITC channel on an LSRII® cytometer (BD Biosciences) prior to and during 60 seconds following the addition of hamster anti-mouse CD3/CD28 monoclonal antibodies (40 µg/ml each) and rat/hamster compBead® (1:50) either alone or in the presence of rat anti-mouse CD31 antibody (clone 390, 10 µg/ml) or in the presence of CD31 peptide 551-574 (100 µM). Negative controls included rat IgG isotype control and scramble peptide. Antibodies and compBeads® were from BD Biosciences.

Plasmon Surface Resonance.

Homophilic binding association and dissociation constants were calculated by surface plasmon resonance (BIAcore® 2000, GE). In brief, peptide 551-574 was coated at 3400 resonance units (RU) on CM5 chips according to the manufacturer's instructions. Soluble peptide 551-574 (12.5, 25, 50 and 100 µM in 200 µl of 10 mM HEPES pH 7.4, 150 mM NaCl, 0.005% Tween 20) was injected at 20 µl/min at 25° C., on the peptide-coated channel and on an uncoated channel. Dissociation was monitored for 300 seconds. Association (kon) and dissociation (koff) constants were calculated using the BIAevaluation® 3.0 Software (GE). Injection of peptide 551-574 on a channel coated with the scramble peptide yielded negligible signal.

Evaluation of Immunoregulation In Vitro.

$CD8^+$ T cell-mediated cytolytic activity against allogeneic mouse aortic smooth muscle cells and measurement of macrophage gelatinase (MMP-2/9) activity were performed as previously described for human cells in Caligiuri et al. (2006 Arterioscler Thromb Vasc Biol 26:618-623) using kits and reagents from Invitrogen. Briefly, primary cultures of FVB/N mouse aorta smooth muscle cells were labelled with the lipophylic tracer DIO (green) and co-cultured for 3 hours with CD8+ T cell-enriched spleen cells from C57Bl/6 mice (n=3 scramble peptide and n=3 peptide 551-574, 50 µM). Cytolysis was evaluated by intracellular accumulation of propidium iodide (PI). Cells were analysed by flow cytometry and the % of cytolysis was calculated by expressing the number of dead (PI+) cells among the target (DIO+) cells. Intracellular MMP-2/9 (gelatinase) activity was measured by flow cytometry in 7-day bone-marrow derived macrophages from C57Bl/6 mice (n=3 scramble peptide and n=3 peptide 551-574, 50 µM) three hours after the incorporation of OregonGreen® gelatine (MFI). T-cell proliferation was performed using either human peripheral blood mononuclear cells of spleen cells from C57Bl/6 ($CD31^{+/+}$) and $CD31^{-/-}$ mice (Charles River France) as previously described (Caligiuri et al. 2005 Arterioscler Thromb Vasc Biol 25:1659-1664). Briefly, cells were plated in triplicates at $0.2 \times 10^6$ cells/well in a U bottom 96-well plate in complete medium (RPMI 1640, 1% pyruvate, 1% glutamine, 1% penicillin-streptomicyne-fungizone, 10% decomplemented fetal calf serum, all from Invitrogen) containing 1 µg/ml anti-mouse CD3/CD28 or 5 µg/ml anti-human CD3 antibodies (BD) as appropriate. CD31 (551-574) and scramble peptide at 25, 50 and 100 µM final concentration were deposited in the wells just before cell plating. Plated cells were cultured for 72 hours in 5% CO2 at 37° C. ($^3H$) thymidine (0.5 µCi/well) was added for the last 16 hours and proliferation evaluated using a Tomtec harvester and analysis on a Wallac micro beta counter. Data are expressed as mean±SEM of cpm in triplicates.

Evaluation of Immunoregulation In Vivo.

Delayed type hypersensitivity (DTH) suppression was evaluated as described in the "Current Protocols in Immunology (2001) 4.0.1-4.0.2 Unit 4.2". Briefly, TNCB (2-chloro-1,3,5-trinitrobenzene, Fluka #79874) was dissolved in acetone/olive oil (1:1 v/v) at a concentration of 10 mg/ml. BALB/c mice (n=6/group) were primed by painting the shaved regions of the abdomen a with a total 0.2 ml of the preparation (n=6/group). The experiment included 3 groups for peptide 551-574 (10, 50, 100 µM) and 1 group treated with scramble peptide at 100 µM). Five days after priming, 10 µl of the TNCB-solvent mixture was painted on the right pinna, 30 minutes after subcutaneous (interscapolar) administration of the peptide 551-574 or the scramble peptide. Ear thickness increases were calculated by subtracting the thickness of the right and the left pinna of each mouse (right-left/left×100), measured at 24 h with a dial caliper ("Pocotest", Kroeplin Längenmesstechnick). The measure was performed 5 times on each ear and averaged for further analysis. The immunosuppressive effect of the peptide was calculated as % suppression=(1−$\Delta$TE/$\Delta$TS)×100, where $\Delta$T=(ear thickness 24 hr after elicitation)−(baseline ear thickness), E=sensitised animals, S=treated animals. Data are expressed as mean±SEM.

Detection of Atherosclerotic Lesion Size and Aneurysm Formation.

Male 28-week old apolipoprotein $E^{-/-}$ mice (n=8-10 mice/group) from our breeding facility were maintained on a regular chow diet and kept under standard conditions. Acceleration of atherosclerosis and aneurysm formation was induced by subcutaneous angiotensin II (Sigma, #A9525) infusion (1 mg/kg/d) for 28 days using osmotic minipumps (Alzet, #2004) as previously described (Daugherty et al. J Clin Invest 105:1605-1612). All experiments were approved by our institutional Ethical committee. Atherosclerotic lesion size was measured as previously described (Caligiuri et al. 2005 Arterioscler Thromb Vasc Biol 25:1659-1664). These experiments were repeated twice with similar results.

Peptides.

All experiments on human material were carried out using the human peptide sequence while the mouse equivalent was used in all mouse experiments. The sequences of the peptides are shown in the table below.

| | | |
|---|---|---|
| Human | NH2 - NHASSVPRSKILTVRVILAPWKK -COOH | SEQ ID NO: 6 |
| Mouse | NH2 - SSMRTSPRSSTLAVRVFLAPWKK -COOH | SEQ ID NO: 5 |
| Scramble | NH2 - SMPAVRSRFSATSLVTLKSRWPK - COOH | SEQ ID NO: 13 |

Example 2: The Apparent Loss of CD31 at the Surface of Blood Lymphocytes is Due to its Shedding Between the 5th and 6th Extracellular Ig-Like Domains In order to establish whether the loss CD31 was restricted to part or extended to the totality of its 6 extracellular Ig-like domains, a multicolor flow cytometry analysis of whole blood leukocytes from 5 healthy donors using two different antibodies specifically recognizing the membrane-distal and membrane-proximal Ig-like domains of the molecule was performed. To be able to discriminate between the different leukocyte populations and assess their state of maturation and activation, a panel of lineage markers as well as the expression of CD45RA and HLA-DR were simultaneously used. While the expression of CD31, as detected by a monoclonal antibody specific for the first domains of CD31 (clone WM-59, dom1-2) was recognized on naïve but not on activated/memory blood T cells, all cells expressed the membrane-proximal extracellular fragment of the molecule detected by another monoclonal antibody specific for the $6^{th}$ Ig-like domain of CD31 (clone PECAM 1.2, dom6), irrespective of their state of maturation/activation (FIG. 2).

Figure 3A:
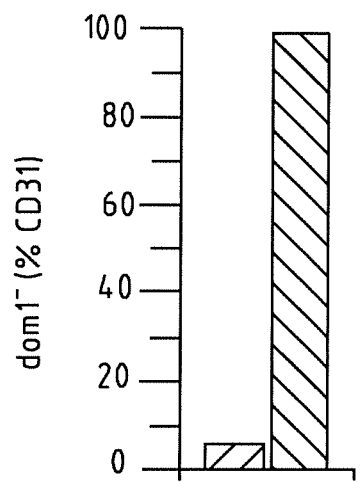
FIG. 3A-B shows that the apparent loss of CD31 on lymphocytes is due to its extracellular shedding. a. Solubilized cell membrane-bound CD31 molecules were extracted from cultured Jurkat CD4+ T cells and coupled to fluorescent beads. The percentage of dom1-bead-bound molecules is <6% in resting conditions and >99% 5' after TCR engagement. b. Most soluble CD31 in culture supernatant (□) of TCR-activated T cells and in human plasma (■) consists of a single truncated fragment comprising dom1-dom5 and lacking dom6. Negligible levels of truncated CD31 lacking both dom5 and dom6 could be detected only in plasma.
Figure 3B:
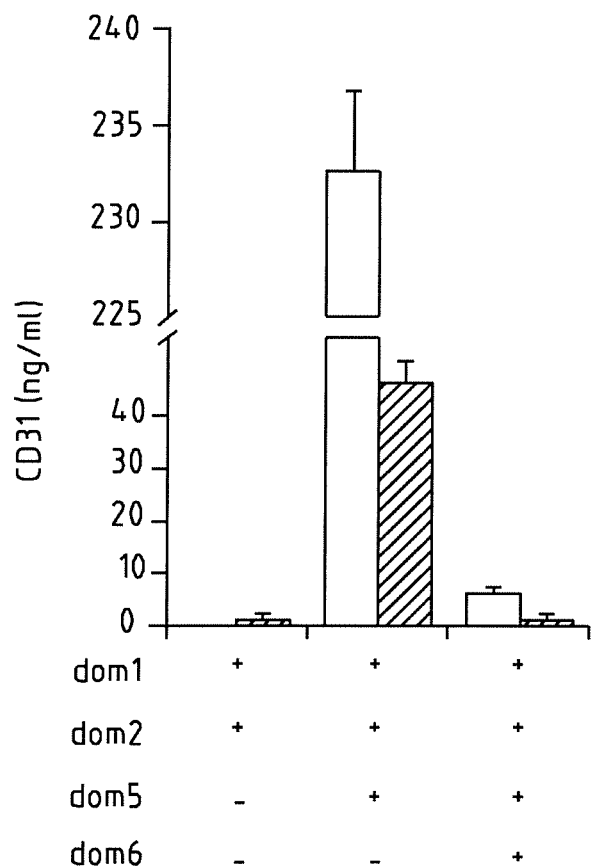

Flow cell cytometry showed that T-cell receptor (TCR) engagement induces a shift of >80% of blood resting T cells from a CD31 dom1$^+$/dom6$^+$ to a dom1$^-$/dom6$^+$ (CD31$^{shed}$) phenotype. Molecular analysis of the membrane proteins from cultured T-cell lysates demonstrated that >99% of the T cell-bound CD31 molecules drop the distal portion containing dom1 already 5' minutes after TCR stimulation in vitro (FIG. 3a). Analysis of the supernatant showed that, simultaneously, a single truncated soluble protein limited to the first 5 Ig-like domains of CD31, accumulates in the culture supernatant (FIG. 3b). Furthermore, the analysis of the plasma of the same healthy donors showed that major part of soluble CD31 in plasma was constituted of a truncated molecule comprising Ig-like domains 1 to 5 and specifically lacking the membrane-proximal $6^{th}$ domain (FIG. 3b) that always remains anchored to the apparently CD31-negative (CD31 dom1$^-$) lymphocytes both in vitro and in vivo. Only a minimal fraction of soluble CD31 contained all 6 extracellular domains predicted in the previously reported (Goldberger et al. J Biol Chem 269:17183-17191) variant spliced form both in culture supernatant and in plasma (FIG. 3b). No significant other cleavage of the molecule occurs upstream of the $5^{th}$ domain since the latter was virtually always present concomitantly with the first domain in the truncated soluble CD31 proteins (FIG. 3b).

Figure 4A:
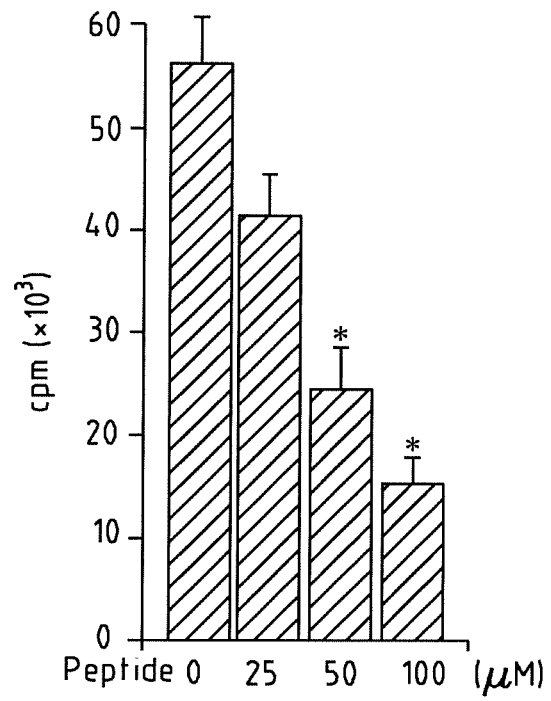
FIG. 4A-B shows that a peptide homotypic of the residual extracellular fragment on CD31$^{shed}$T induces CD31-ITIM phosphorylation. a. Proliferative response to TCR engagement of human peripheral blood mononuclear cells in the presence of increasing doses of CD31 peptide 551-574. *p<0.05 vs dose "0". b. Flow cytometry assessment of 686ITIM phosphorylation on solubilized membrane-bound CD31 from cultured Jurkat CD4+ T cells. Solubilized proteins were captured by E9-PECAM-1.2 (dom6) functional CBA beads and detection was carried out by anti-pY686 rabbit sera followed by AlexaFluor®488-anti-rabbit secondary antibody. The histogram shows the Median Fluorescent Intensity (MFI)±the % of the variability coefficient (CV %) of Alexafluor®488 (pY686) over 2000 E9-PECAM-1.2 acquired beads. Pervan=positive control (pervanadate); CD3/CD28=anti-CD3 and anti-CD28 antibodies (1 µg/ml each); peptide=CD31 peptide 551-574 (100 µM).
Figure 4B:
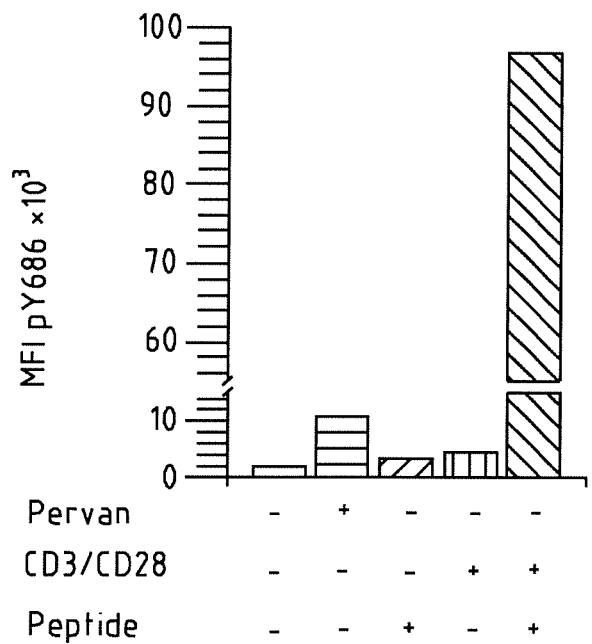

Example 3: A Peptide Contained in the Residual Extracellular CD31 Fragment on CD31$^{shed}$ T Cells Enhances Phosphorylation of CD31-ITIM A CD31 dom6-derived synthetic peptide corresponding to the juxta-membrane 23 aminoacids (551-574) of the ectodomain of the human molecule binds both to CD31 dom1$^+$ and to CD31 dom1$^-$ (CD31$^{shed}$) CD4$^+$ T lymphocytes ex vivo. Importantly, the binding of this peptide on T cells has functional consequences on immune cell control since it exerted dose-dependent inhibition of human peripheral blood T-cell proliferation in vitro (FIG. 4a). To assess whether the inhibitory effect of the peptide could be mediated by homophilic binding and engagement of the CD31 signaling, the level of phosphorylation of the CD31 ITIM tyrosine at position 686 ($_{686}$ITIM) in cultured T cells was evaluated. Stimulation of the TCR by anti-CD3 and anti-CD28 antibodies alone or the sole presence of the peptide induced a minor increase of CD31 pY686 (FIG. 4b) but concomitant TCR-stimulation in the presence of the peptide boosted the phosphorylation the CD31$_{686}$ITIM by a factor of >23 (FIG. 4b).

Example 4: CD31 Homotypic Peptide 551-574 Inhibits a Large Array of Cell-Mediated Immune Responses In Vitro and In Vivo To further test our hypothesis, in vivo experiments were performed, and the murine equivalent of CD31 (551-574) peptide was therefore synthesized. Its properties were evaluated in vitro and in vivo. Its homophilic interaction by surface plasmon resonance analysis was first established (FIG. 5a). The association and dissociation constants were of 134±120 M$^{-1}$s$^{-1}$ and 1.58E-03±1.07E-03 s$^{-1}$, respectively and the affinity at equilibrium was 17.8±9.7 μM, in agreement with previous measurement done on recombinant human CD31 homo-dimerization using other systems. It was next assessed whether the mouse CD31 (551-574) peptide was able to inhibit calcium mobilization in response to the co-engagement of the CD3 and of the co-stimulatory molecule CD28 in spleen lymphocytes. The data showed that homophilic targeting of the juxta-membrane portion of CD31 whit this small peptide is as an efficient immunoregulatory strategy as it is the co-ligation of CD3 and CD28 with the distal portion of CD31 by cross-linking the molecules using specific monoclonal antibodies (FIG. 5b). The engagement of the CD31 molecular pathway by this peptide could attain effective suppression of antigen-driven lymphocyte responses in vitro and in vivo. It was found that peptide 551-574 inhibits in a dose-dependent manner the proliferation of spleen cells in response to stimulation of the T cell-receptor in vitro (FIG. 5c). At low dose, the effect of the peptide was exclusively due to its homophilic binding with CD31 molecules since no effect was observed on spleen cells from CD31$^{-/-}$ mice (FIG. 3c). However, at high concentrations the peptide can also bind to other (low affinity) heterophilic ligands as suggested by its effect at 100 μM dose also on cells lacking CD31 (FIG. 5c). The scramble peptide, used at the highest dose, was ineffective (FIG. 5c). Finally, the therapeutic immunosuppressive potential of this peptide in vivo in the context of matched, histocompatible antigen-driven immune responses was evaluated using a model of delayed type of hypersensitivity. Distal recall of an hapten-elicited specific immune response was suppressed in a dose-dependent manner by peptide 551-574 in this model (FIG. 5d). Effective immunosuppression was achieved by a single subcutaneous administration of 50 μM of the peptide 551-574 while the scramble peptide was ineffective (FIG. 5d).

Figure 6A:
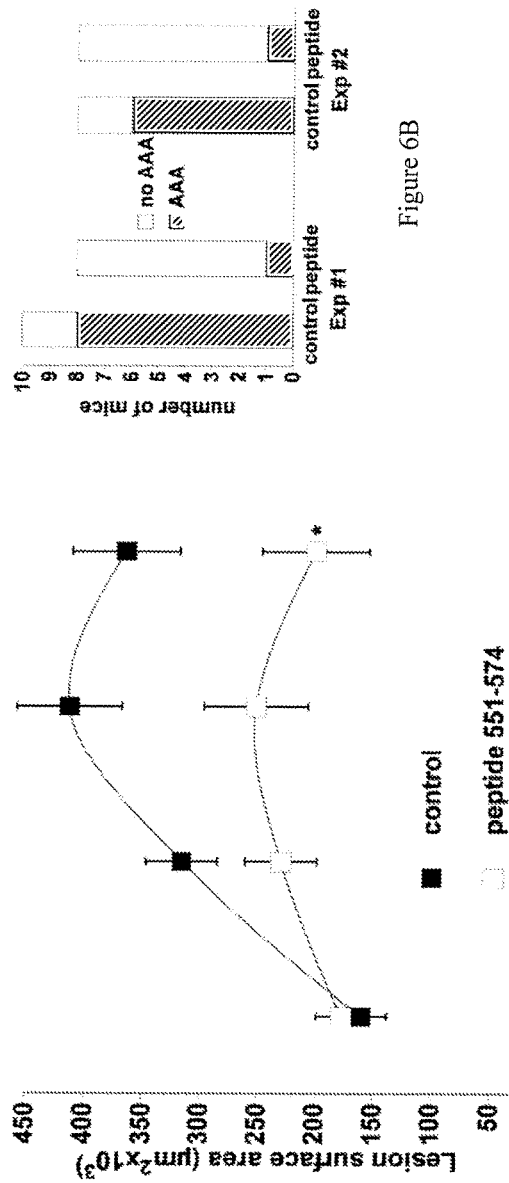
FIG. 6A-C shows that CD31 peptide biotherapy prevents acceleration of atherosclerosis and aneurysm formation. a. Mean±SEM of Atherosclerotic lesion surface area in serial cross-sections of the aortic root at 200, 400, 600, 800 µm from the appearance of the first cusp in control (■) and peptide 551-574 (□) treated mice. *p<0.05 vs control, ANOVA, repeated measure. b. The presence of an abdominal aortic aneurysm (AAA) was macroscopically, blindly evaluated by A.G. and A. N. after careful dissection of the adventitial tissue. An aneurysm was present in 8/10 (Exp #1) or 6/8 (Exp #2) control mice as opposed to only 1/8 peptide-treated mice in both experiments (p<0.001 by Chi squared test). The images below show an example of aneurysm (AAA; arrows) as compared to the absence of aneurysm (no AAA) of the abdominal aorta. c. Flow cytometry analysis of the effect of the peptide (50 µM) on CD8+ T cell (% cytolysis) and macrophage (MMP-2/9 activity) functions. Data represent mean±SEM of cultures from 3-4 mous/group. *p<0.05 vs control.
Figure 6B:
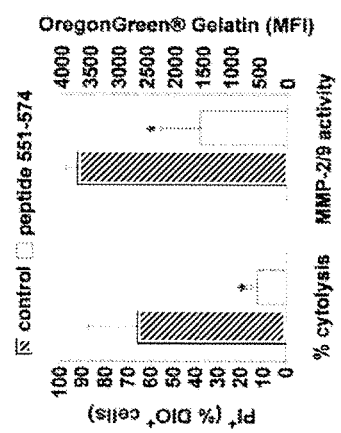
Figure 6C:
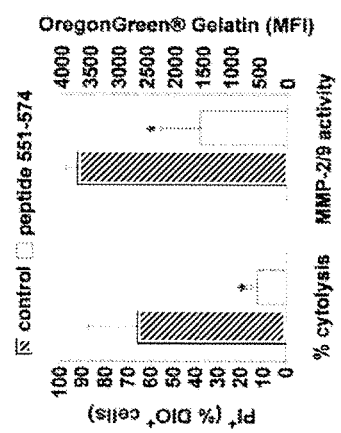

Example 5: CD31$^{shed}$ Cell-Targeting Peptide Biotherapy Prevents Disease Progression and Aneurysm Formation in Atherosclerotic Mice The model of angiotensin II infusion into aged apolipoprotein E−/− mice (25) was used, this model closely mimicking atherothrombosis in humans. Daily subcutaneous administration of 50 μM of the peptide prevented both the acceleration of plaque growth in the aortic root (FIG. 6a) and the formation of atherothrombotic abdominal aortic aneurysms (AAA) in this model (FIG. 6b). in vitro, the CD31-derived peptide 551-574 inhibited both the activity of matrix degrading enzymes in bone-marrow derived macrophages and CD8$^+$ T cell-dependent cytolysis of murine aortic smooth muscle cells (FIG. 6c).

Example 6: In Silico and In Vitro Validation of the 10 Amino Acid-Long Peptide Candidate Peptide "PepReg"

A shorter nested peptide corresponding to the ten COOH terminal amino acids was tested. This peptide is shown as SEQ ID NO: 3 and referred to as "PepReg". As shown in the table below, this peptide was expected to be more stable than the CD31 551-574 peptide of 23 amino acids.

TABLE

Characteristics of PepReg vs the 23aa CD31 peptide in silico

| | PepReg CD31 564-574 (10aa) | CD31 551-574 (23aa) |
|---|---|---|
| sequence | VRVFLAPWKK (SEQ ID NO: 3) | SSMRTSPRSSTLAVRV FLAPWKK (SEQ ID NO: 5) |
| Number of amino acids | 10 | 23 |
| Molecular weight | 1243.5 | 2606.0 |
| Theoretical pI | 11.17 | 12.31 |
| Formula | C62H98N16O11 | C116H193N35O31S1 |
| − (Asp, Glu) /+ (Arg, Lys) charges | 0/3 | 0/5 |
| Instability index | 25.38 | 65.09 |
| Estimated half-life (mammalian reticulocytes, in vitro) | 100 hours | 1.9 hours |
| Aliphatic index | 107.00 | 68.83 |

The immunosuppressive properties of PepReg (10aa) vs the 23 aa parent peptide were evaluated in vitro. Negatively purified CD4+ cells from C57Bl6 mice were stimulated by soluble anti-CD3 purified antibodies and bone marrow derived dendritic cells. Cells from triplicate wells were analyzed for the expression of the early activation marker CD69 after 18 hours culture in complete RPMI medium supplemented with 10% fetal calf serum. Flow cytometry showed that PepReg was at least as efficient as the 23aa peptide in suppressing T cell activation as determined by the percentage of CD4 cells expressing CD69. Interestingly, the effect was more reproducible (smaller standard deviation) and was observed with lower doses (50 μg/ml vs 100 μg/ml) of PepReg (10aa) as compared to the parent (23aa) peptide. The suppression of T cell proliferation by PepReg was analyzed by [H3] thymidin incorporation and persisted up to 7 days of culture at 37° C. in 10% serum demonstrating that the data regarding the stability of the peptide obtained in sifico were validated in vitro.

Example 7: In Vivo Validation of the 10 Amino Acid-Long Peptide Candidate Peptide "PepReg" in the EAE Model Experimental Autoimmune Encephalomyelitis (EAE), also called Experimental Allergic Encephalomyelitis, is an animal model of Multiple Sclerosis.

Twelve-week old female C57BL/6J mice were immunized with 300 μg of MOG35-55 peptide emulsified in Complete Freund's Adjuvant 1:1 by volume containing 800 μg of nonviable desiccated *Mycobacterium tuberculosis* H37RA. A final volume of 200 μl of the emulsion was injected subcutaneously at 4 sites (50 μl/site) over the flanks. In addition, 300 ng of Pertussis toxin was injected intravenously (retro-orbital plexus) on the same day and 2 days later. Clinical signs of EAE ware assessed daily by the following scoring system: 0, no signs; 1, hindlimb weakness; 2, hindlimb weakness and tail paralysis; 3, hindlimb and tail paralysis; 4, hindlimb and tail paralysis and forelimb weakness; 5, moribund state; and 6, death. The peak (waxing phase) occured around day 21. In this C57BL/6J mouse model, there was no waning phase as assessed in our laboratory up to day 41.

The experiment was carried out with ten mice per group. The mice of each group were treating with either of:
PBS;
PepReg (SEQ ID NO: 3); or
PepScra (SEQ ID NO: 14).

The dosing was of 50 μg of peptide per mice and per day (i.e. about 2 mg/Kg per day). The peptide was administered by a subcutaneous injection.

Disease protection was associated with reduced infiltration of IL17+ and IFNg+ T helper CD4+ cells and increased proportion of regulatory CD25+/foxP3 CD4+ cells in the central nervous system of the mice.

Figure 7:
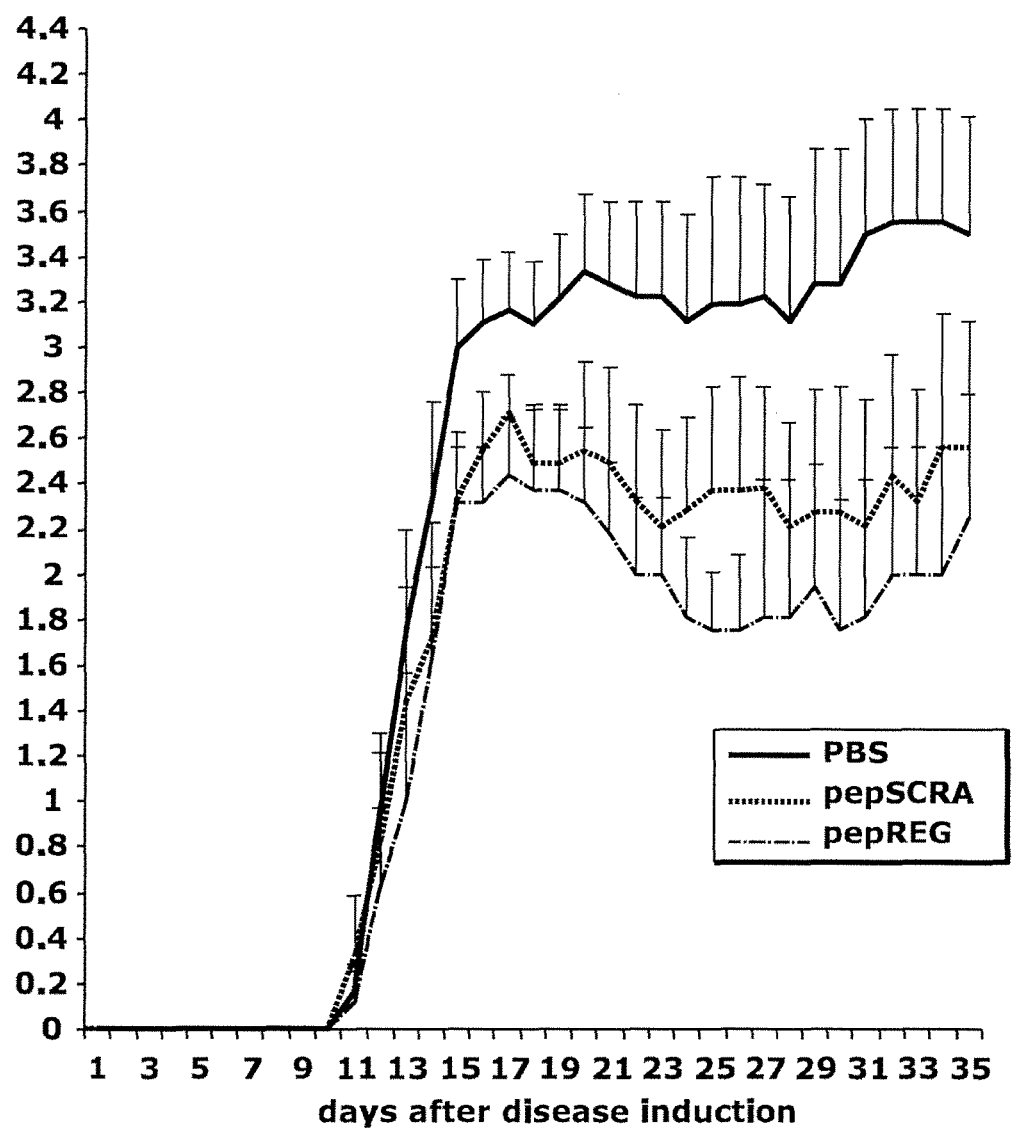
FIG. 7 shows the clinical score of EAE activity (paralysis level). "pepREG" refers to the peptide of SEQ ID NO: 3. "pepSCRA" refers to the peptide of SEQ ID NO: 14.

As shown on FIG. 7, PepReg is capable of arresting disease development in the waxing phase (Day 15) and reducing disease extension in the plateau phase (Days 21 through to 35).

The scrambled peptide was also beneficial, although less than PepReg. This result suggests that the amino acid composition rather than the sequence per se is important for the beneficial effect. This result has important implications for the development of peptidomimetics.

Example 8: Detection of Shed CD31 in Plasma from Patients Suffering from Atherothrombosis and in Unaffected Individuals The total amount of CD31, the amount of shed CD31 and the amount of spliced CD31 has been measured both in eleven individuals suffering from atherothrombosis and in twenty-three unaffected individuals.

The group "Atherothrombosis" comprised eleven individuals suffering from chest pain even at rest and presenting an abnormal coronarography.

The group "No Atherothrombosis" comprised twenty-three individuals. A sub-analysis was carried out on the group "No Atherothrombosis", which was found to comprise:
eight individuals presenting a normal coronarography and a normal carotid echodoppler in spite of chest pain;
four individuals presenting a normal coronarography in spite of chest pain, but in whom atherosclerosis was detected by carotid echodoppler; and
eleven individuals suffering from chest pain only on effort and presenting an abnormal coronarography (i.e. suffering from coronary atherosclerosis without thrombosis).

The total amount of CD31, the amount of shed CD31 and the amount of spliced CD31 was determined as follows.

1. The total amount (1 μl/test) of beads (E9, coupled with clone JC70A, DAKO) was transferred to a conical tube and centrifuged at 200 g for 5 minutes. The supernatant was carefully discarded and replaced with same amount of serum enhancement buffer (BD #51-9002150), and incubated at room temperature for 15 minutes.

2. The fluorescently-labeled antibody antibody mix (PE-WM59; FITC-HC1/6; PB-PECAM1.2) was prepared, each at 1 μg/ml, 1 μl each/condition.

3. 1 tube precondition was prepared, each containing 3 μl of a standard dilution or a plasma sample. The reconstituted beads were centrifuged at 200 g for 5 minutes, the supernatant was discarded and the serum enhancement buffer was replaced with the fluorescently-labeled antibody mix. 3 μl of this solution was distributed in each of the tubes containing the standard dilution and samples, and the solution incubated for 1 hour at 4° C. in the dark.

4. 150 μl of Washing buffer (BD #51-9003797) were added to each tube, and the signal was acquired.

As shown in the table below, the percentage of shed CD31 was higher in individuals suffering from atherothrombosis than in unaffected individuals, in spite of the fact that all individuals were suffering from chest pain.

| CD31 Plasma Level (ng/ml) | total | splice | shed |
| --- | --- | --- | --- |
| Atherothrombosis (n = 11) | 11.55 ± 0.7 | −7.02 ± 2.69 | 18.57 ± 2.67 |
| No Atherothrombosis (N = 23) | 11.58 ± 0.49 | 5.26 ± 1.850 | 6.31 ± 1.85 |
| T-test Prob >F | 0.9756 | 0.0007 | 0.0006 |

Total CD31 amounts were similar in the four groups, while the amount of shed CD31 and the amount of spliced CD31 were significantly different in each paired group comparison. Shed CD31 was increased in individuals with abnormal coronarography, with highest values in those suffering from atherothrombosis. Splice CD31 was still present in patients suffering from atherosclerosis without atherothrombosis, while it was almost undetectable in patients suffering from atherothrombosis.

These results demonstrate that high levels of CD31 soluble splice variants associated with low levels of shed CD31 indicates that the patient suffers from non specific chest pain, eventually associated with carotid plaques. A slight increase of shed CD31 levels associated with normal or reduced levels of CD31 soluble splice variants indicates that the patient suffers from atherosclerosis. An important increase of shed CD31 levels associated with undetectable amounts of CD31 soluble splice variants indicates that the patient suffers from atherothrombosis.

Example 9: Discussion of the Results

Dysimmune diseases are linked to lack of appropriate control of immune responses. Atherosclerosis and its complications are not only due to metabolic disturbances but are increasingly recognized as a dysimmune disease and an important current issue is the identification of interventional tools able to restore immunoregulation. It has been previously shown that atherothrombotic manifestations such as plaque rupture and thrombosis (Caligiuri et al. 2005 Arterioscler Thromb Vasc Biol 25:1659-1664) or aneurysm complication (Caligiuri et al. 2006 Arterioscler Thromb Vasc Biol 26:618-623) are associated with a significant reduction of CD31+ T lymphocytes in the peripheral blood. In these previous works, we documented that lack of CD31 signaling on lymphocytes elicited pro-atherothrombotic immune responses whilst the presence of CD31 on T cells was able to inhibit them.

Here it is demonstrated that the assumed loss of the molecule on activated/memory T lymphocytes is actually incomplete and results from shedding of CD31 between the 5th and 6th extracellular Ig-like domains. CD31 shedding occurred immediately after cell activation on T lymphocytes and was accompanied by the accumulation of the truncated molecule in the supernatant together with trace levels of the spliced variant produced by the cells. This finding was unsuspected because all commercially available tests to detect plasma CD31 use antibodies directed to CD31 domains 1 to 5, and therefore cannot discriminate between the spliced variant (containing all the 6 extracellular domains) and the truncated (domains 1 to 5) forms of CD31. The subtractive immunosorbent assay described herein is able to discriminate between the two forms of soluble CD31 and precisely quantify the proportion of each of them in the plasma. This assay showed that the major part of plasma CD31 comprises domains 1 to 5 but lacks the membrane-proximal 6th domain, which remains anchored to blood CD31 dom1-lymphocytes. Therefore, it is proposed to refer to these lymphocytes as CD31shed rather that CD31 "negative" cells. Previous work in vitro had indicated that CD31 shedding at an unidentified position N-terminal from the transmembrane segment of the molecule can occur in endothelial cells undergoing apoptosis (Ilan et al. 2001. Faseb J 15:362-372). For the first time, it is shown herein that shedding is responsible for the CD31 (incomplete) loss on blood lymphocytes and that the circulating CD31 consists mainly of a truncated form derived from its cleavage between the Ig-like domains 5 and 6, rather than of the secreted spliced variant form. Genetic polymorphisms for CD31 have been described, but the predictive value of soluble CD31 levels was conflicting either in atherothrombosis or other dysimmune diseases. In fact, while the amount of the spliced form can be predicted by different genetic variants, the proportion of the form resulting from protein shedding is not determined by CD31 gene polymorphism. It is proposed that the disparity between the different studies was due to fact that circulating CD31 is a mixture of the genetic variant and of the truncated form and discrimination between the two forms of CD31 was not possible. The subtractive method described herein will allow the differentiation of the prognostic value determined by genetic variants of CD31 independently of that linked to CD31 shedding.

The fact that CD31 is not completely lost on blood lymphocytes offers a unique opportunity to rescue its physiological immunoregulatory function by targeting the residual extracellular portion of the molecule. Indeed, it has been documented herein that this can be achieved by a homotypic peptide-based therapy, both in vitro and in vivo. Homophilic binding of this peptide dramatically enhanced the phosphorylation the CD31 686ITIM and inhibited their TCR-induced proliferation. Induction of CD31 ITIM phosphorylation by antibody-mediated cross-linking of CD31 and CD3 surface molecules was previously known to inhibit calcium mobilization induced by anti-CD3 antibodies in human T-cell lines. Remarkably, it has been found that targeting the juxta-membrane portion of CD31 whit the small homotypic peptide is as an efficient immunoregulatory strategy as it is the co-ligation of CD3 and CD28 with the distal portion of CD31 by cross-linking the molecules with antibodies. A selective small synthetic peptide strategy is obviously simpler and might also be safer than using large proteins, such as monoclonal antibodies and cross-linkers, for the biotherapy of immunological disorders (Isaacs 2007. Curr Opin Pharmacol 7:418-425).

With this idea in mind, it was assessed whether the engagement of the CD31 molecular pathway by this peptide could attain effective suppression of antigen-driven lymphocyte responses in vitro and in vivo in the context of matched, histocompatible antigen-driven immune responses. Distal recall of an hapten-elicited specific immune response was suppressed in a dose-dependent manner by a single subcutaneous administration of the peptide. A similar protective effect of a single peptide shot was also observed in experimental autoimmune encephalomyelitis (a mouse model of multiple sclerosis) and lasted for up to 5 days.

Consequently, it was evaluated whether rescuing of CD31-mediated immunoregulation by the synthetic peptide 551-574 could be employed in a biotherapy to fight atherothrombosis since CD31-mediated immunoregulation is typically lost in this disease. It was chosen to use the angiotensin-induced model of atherothrombosis because the abrupt acceleration of atherosclerotic plaque growth and the development of abdominal aortic aneurysms complicated by a thrombus in this model are produced simply by excess bioavailability of a physiological peptide—angiotensin II—and does not require the use of surgery, gene transfer or high fat diet, each of which could considerably bias the interpretation of the results. The CD31-peptide prevented both the acceleration of plaque growth in the aortic root and the formation of atherothrombotic abdominal aortic aneurysms in this model. Such a dramatic protective effect was superior to any therapeutic molecule ever tested and equivalent to that achieved by genetic manipulation.

Macrophages and lymphocytes represent the most important immune cells involved in the development of atherothrombosis. The local function of these cells injure the cellular and extracellular components of the arterial layers resulting in either plaque rupture and luminal thrombosis, when occurring in the fibrous cap of atherosclerotic plaques, or aneurysm formation and eventually rupture, when happening in the outer layers of the artery. Degradation of the extracellular matrix is essentially due to the activity of macrophage-derived matrix metalloproteases while death of arterial smooth muscle cells is putatively caused by T cell-mediated cytolysis. Remarkably, CD31+ T lymphocytes exert an important immunosuppressive function on both these phenomena which are conversely aggravated by CD31shed T cells. An aberrant reduction of CD31+ cells in patients with atherothrombosis underlies the defective immunoregulation observed in the disease. Here it is shown that the CD31-derived peptide 551-574 inhibits both the activity of matrix degrading enzymes and T cell-dependent cytolysis of the arterial wall cells. The immunoregulation conveyed by this peptide is as efficient as that exerted by immunoregulatory CD31+ T cells and hence may counterweight the loss of the physiologic CD31-dependent immunoregulation in human atherothrombosis.

This is the first time that a peptide-based biotherapy is envisaged to correct the defective immunoregulation characteristic of atherothrombosis and prevent development of the disease in patients. In addition, such biotherapy may broaden over to other debilitating dysimmune diseases. In particular, experimental studies have suggested that CD31-signalling might play a protective role in rheumatoid arthritis (Wong et al. 2005. J Clin Immunol 25:19-28), multiple sclerosis (Graesser et al. 2002. J Clin Invest 109:383-392) and non-alchoolic fatty liver disease (Goel et al. 2007. Am J Physiol Gastrointest Liver Physiol 293:G1205-1214).

Example 10: Evaluation of Ninety Six Peptides According to the Invention

The ninety six peptides consisting of a fragment having a sequence selected from the group consisting of:
  amino acids 2 to 23, 3 to 23, 4 to 23, 5 to 23, 6 to 23, 7 to 23, 8 to 23, 9 to 23, 10 to 23, 11 to 23, 12 to 23, 13 to 23, 14 to 23, 15 to 23, 16 to 23, 17 to 23, 18 to 23, 19 to 23, 20 to 23 and 21 to 23 of SEQ ID NO: 5; and
  amino acids 2 to 23, 3 to 23, 4 to 23, 5 to 23, 6 to 23, 7 to 23, 8 to 23, 9 to 23, 10 to 23, 11 to 23, 12 to 23, 13 to 23, 14 to 23, 15 to 23, 16 to 23 and 17 to 23 of SEQ ID NO: 6; and amino acids 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4 and 1 to 3 of SEQ ID NO: 5; and amino acids 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4 and 1 to 3 of SEQ ID NO: 6; and amino acids 2 to 22, 3 to 21, 4 to 20, 5 to 19, 6 to 18, 7 to 17, 8 to 16, 9 to 15, 10 to 14 and 11 to 13 of SEQ ID NO: 5; and amino acids 2 to 22, 3 to 21, 4 to 20, 5 to 19, 6 to 18, 7 to 17, 8 to 16, 9 to 15, 10 to 14 and 11 to 13 of SEQ ID NO: 6;

are tested for confirming that these peptides induce CD31-ITIM phosphorylation. CD31-ITIM phosphorylation is assessed by studying the effect of increasing doses of the peptides according to the invention on CD31-ITIM phosphorylation of cultured Jurkat cells stimulated with anti-CD3 and/or anti-CD28 antibodies, as described in Example 3.

It is confirmed that the above peptides inhibit T-cell proliferation using the protocol described by Caligiuri et al. (2005 Arterioscler Thromb Vasc Biol 25:1659-1664).

It is confirmed that the peptides can achieve effective immunosuppression using the protocol described in the Current Protocols in Immunology (2001, 4.0.1-4.0.2 Unit 4.2).

The efficiency of the peptides for treating a thrombotic disorder is confirmed in the model of angiotensin II infusion into aged apolipoprotein E−/− mice, which closely mimicks atherothrombosis in humans.

The efficiency of the peptides for treating an autoimmune disorder is confirmed in the Experimental Autoimmune Encephalomyelitis (EAE) model, which is an animal model of Multiple Sclerosis, and in a model for rheumatoid arthritis.

Example 11: Evaluation of the Peptides According to the Invention in an Animal Model of the Rheumatoid Arthritis (RA)

It is confirmed that the peptides according to the invention (e.g. PepReg and/or the peptides described in Example 10) are capable of arresting disease development and/or reducing disease extension in an animal model of Rheumatoid arthritis (RA).

Rheumatoid arthritis (RA) is a chronic and systemic inflammatory autoimmune disorder that causes the immune system to attack the joints. The disease is characterized by aggressive synovial hyperplasia (pannus formation) and inflammation (synovitis), which, if left untreated, lead to progressive destruction of joint cartilage and bone. The destructive lesions result from both immune responses and non-antigen-specific innate inflammatory processes. Several studies have shown that CD31 plays a critical role in this disease since the disease onset and progression is accelerated in its absence.

DBA/1 mice are used in this experiment. Induction of RA is initiated on 12 week-old mice. On day 0, mice are immunized intradermally at the base of the tail with 150 μg of bovine type II collagen (CII) emulsified with an equal volume of Freund's complete adjuvant containing 200 μg of H37RA Mycobacterium tuberculosis. On day 21, mice are given a booster (intradermal injection of 150 μg of bovine CII in Freund's incomplete adjuvant). Simultaneously, mice receive an intravenous injection of 50 μg of LPS. Mice are followed up for two months. Following immunization, the animals develop an autoimmune polyarthritis that is characterized by severe cartilage and bone erosions. Mouse collagen-induced RA shares several clinical, histopathological and immunological features with human RA.

The peptides according to the invention are administered following one of the below treatment schemes.

Scheme 1: Preventive administration. Two doses (50 and 100 mg/kg) of the peptide is administered to the mice one day before the CII immunization and than either daily, or twice a week, or weekly, for the study period (2 months). A peptide with a scrambled sequence (i.e. a peptide comprising the same amino acids as the peptide according to the invention, but not the same sequence) is administered to a control group of mice. Treatment is pursued for one month.

Scheme 2: Curative administration. The peptide (50 and 100 mg/kg) and the scramble peptide are administered to mice after the beginning of the symptoms, either daily, or twice a week or weekly until the end of the study. Equivalent groups of mice are kept in conventional housing facilities and are bled weekly from a tail vein to monitor bleeding time and specific pathogen antibody raise in sera (CDTA, Orleans).

Arthritis development is monitored by physical examination 3 times per week. Inflammation in each of the 4 paws is graded on a scale of 0 to 3, and the scores for the 4 paws will be cumulated (yielding a maximum score of 12 per mouse). The arthritis index is calculated by dividing the total score in the experimental mice by the number of arthritic mice.

Lesions in the joints are also followed. Ankle joints of mice are excised 6 weeks after immunization and fixed in 10% buffered formalin, decalcified in 10% EDTA, embedded in paraffin, sectioned, and stained with hematoxylin and eosin. The intensity of synovial hyperplasia, cellular inflammation, and pannus formation is evaluated, and arthritis is graded in a blinded manner on a scale of 0 to 4.

Immunohistochemistry is further used to track and to phenotype inflammatory cells infiltrated in the joints.

The immunoregulation status is evaluated by measuring levels of serum IgG1 and IgG2a to CII. The measurement is performed by enzyme-linked immunosorbent assay (ELISA). The proliferation of T cells isolated from draining lymph nodes and the spleen is tested by the incorporation of $^3$H thymidine in response to CII-loaded dendritic cells.

Cell populations in the lymphoid organs and in the synovia is analyzed by flow cytometry.

This experiment allows confirming that continuous administration of the peptides according to the invention prevents onset of RA. The curative phase allows evaluating the therapeutic potential of the peptides for treating RA in patients that do not respond to the current biologicals (i.e. 40% of the patients). Dose and frequency of the administrations able to drive a regression of the inflammatory cells in the joints, and regression of the clinical score, are also determined.

The invention claimed is:

1. An isolated peptide of 6 to 15 amino acids consisting of:
   a) a fragment of 6 to 15 amino acids of sequence SEQ ID NO: 6; or
   b) a fragment of 6 to 15 amino acids of sequence SEQ ID NO: 5 corresponding to (a) in murine CD31; and
   wherein said peptide comprises or consists of an amino acid sequence selected in the group consisting of SEQ ID Nos 2, 3, 4, 22, 23, 24, 25, 26, 27, 28, 29, 39, 40, 41, 42, 43, 44, 45, 46, 53, 54, 55, 56, 57, 58, 59, 60, 61, 62, 72, 73, 74, 75, 76, 77, 78, 79, 80, 81, 87, 88, 89, 90, 91, 96, 97, 98, 99 and 100.

2. The peptide according to claim 1, wherein said peptide consists of any one of SEQ ID NOs: 2, 3 or 4.

3. The peptide according to claim 1, wherein said peptide comprises at least one chemical modification improving its stability and/or its bioavailability and wherein said at least one chemical modification improving its stability and/or its bioavailability is selected from the group consisting of:
   (a) modification to the N-terminal and/or C-terminal end of the peptide by N-terminal acylation or deamination;
   (b) modification of the C-terminal carboxyl group into an amide or an alcohol group;
   (c) modification at the amide bond between two amino acids by acylation or alkylation at the nitrogen atom or the alpha carbon of the amide bond linking said two amino acids;
   (d) modification at the alpha carbon of the amide bond linking two amino acids by acylation or alkylation at the alpha carbon of the amide bond linking said two amino acids;
   (e) replacement of one or more naturally occurring L-enantiomeric amino acids with a corresponding D-enantiomer;
   (f) retro-inversion, in which one or more naturally occurring L-enantiomeric amino acids is replaced with a corresponding D-enantiomer, together with inversion of the amino acid chain;
   (g) replacement of one or more alpha carbons with nitrogen atoms; and
   (h) binding of the amino group of one or more amino acid to the β carbon instead of the α carbon.

4. A pharmaceutical composition comprising one or more of
   a peptide of 6 to 15 amino acids consisting of
   a) a fragment of 6 to 15 amino acids of sequence SEQ ID NO: 6; or
   b) a fragment of 6 to 15 amino acids of sequence SEQ ID NO: 5 corresponding to (a) in murine CD31; and
   wherein said peptide comprises or consists of an amino acid sequence selected in the group consisting of SEQ ID Nos 2, 3, 4, 22, 23, 24, 25, 26, 27, 28, 29, 39, 40, 41, 42, 43, 44, 45, 46, 53, 54, 55, 56, 57, 58, 59, 60, 61, 62, 72, 73, 74, 75, 76, 77, 78, 79, 80, 81, 87, 88, 89, 90, 91, 96, 97, 98, 99 and 100,
   a nucleic acid encoding said peptide; and
   a physiologically acceptable carrier.

5. A method of activating or restoring CD31-mediated signaling in an individual in need thereof, comprising administering to the individual a peptide of 6 to 15 amino acids consisting of:
   a) a fragment of 6 to 15 amino acids of sequence SEQ ID NO: 6; or
   b) a fragment of 6 to 15 amino acids of sequence SEQ ID NO: 5 corresponding to (a) in murine CD31; and
   wherein said peptide comprises or consists of an amino acid sequence selected in the group consisting of SEQ ID Nos 2, 3, 4, 22, 23, 24, 25, 26, 27, 28, 29, 39, 40, 41, 42, 43, 44, 45, 46, 53, 54, 55, 56, 57, 58, 59, 60, 61, 62, 72, 73, 74, 75, 76, 77, 78, 79, 80, 81, 87, 88, 89, 90, 91, 96, 97, 98, 99 and 100.

6. A method of claim 5, wherein said method is a method for treating a thrombotic or an autoimmune disorder in said individual and wherein said individual has a thrombotic or an autoimmune disorder.

7. The method according to claim 5, wherein said individual has a CD31⁻T lymphocytes phenotype.

8. The method according to claim 5, wherein said peptide comprises at least one chemical modification improving its stability and/or its bioavailability and wherein said at least one chemical modification is selected from the group consisting of:
   (a) modification to the N-terminal and/or C-terminal end of the peptide by N-terminal acylation or deamination;
   (b) modification of the C-terminal carboxyl group into an amide or an alcohol group;
   (c) modification at the amide bond between two amino acids by acylation or alkylation at the nitrogen atom or the alpha carbon of the amide bond linking said two amino acids;
   (d) modification at the alpha carbon of the amide bond linking two amino acids by acylation or alkylation at the alpha carbon of the amide bond linking said two amino acids;
   (e) replacement of one or more naturally occurring L-enantiomeric amino acids with a corresponding D-enantiomer;
   (f) retro-inversion, in which one or more naturally occurring L-enantiomeric amino acids is replaced with a corresponding D-enantiomer, together with inversion of the amino acid chain;
   (g) replacement of one or more alpha carbons with nitrogen atoms; and
   (h) binding of the amino group of one or more amino acid to the β carbon instead of the α carbon.

9. The method according to claim 6, wherein said disorder is a thrombotic disorder selected from the group consisting of atherothrombosis, atherosclerosis, acute coronary syndrome, ischemic stroke, peripheral arterial disease and abdominal aortic aneurysm.

10. The method according to claim 6, wherein said disorder is an autoimmune disorder selected from the group consisting of rheumatoid arthritis, multiple sclerosis, inflammatory bowel disease, systemic lupus erythematosus, Graves' disease and diabetes mellitus.

11. The method according to claim 6, wherein said individual has a CD31⁻T lymphocytes phenotype.

12. The method according to claim 6, wherein said peptide comprises at least one chemical modification improving its stability and/or its bioavailability and wherein said at least one chemical modification is selected from the group consisting of:
   (a) modification to the N-terminal and/or C-terminal end of the peptide by N-terminal acylation or deamination;
   (b) modification of the C-terminal carboxyl group into an amide or an alcohol group;
   (c) modification at the amide bond between two amino acids by acylation or alkylation at the nitrogen atom or the alpha carbon of the amide bond linking said two amino acids;
   (d) modification at the alpha carbon of the amide bond linking two amino acids by acylation or alkylation at the alpha carbon of the amide bond linking said two amino acids;
   (e) replacement of one or more naturally occurring L-enantiomeric amino acids with a corresponding D-enantiomer;
   (f) retro-inversion, in which one or more naturally occurring L-enantiomeric amino acids is replaced with a corresponding D-enantiomer, together with inversion of the amino acid chain;
   (g) replacement of one or more alpha carbons with nitrogen atoms; and
   (h) binding of the amino group of one or more amino acid to the $\beta$ carbon instead of the $\alpha$ carbon.

13. The pharmaceutical composition according to claim 4, wherein said peptide comprises at least one chemical modification improving its stability and/or its bioavailability and wherein said at least one chemical modification is selected from the group consisting of:
   (a) modification to the N-terminal and/or C-terminal end of the peptide by N-terminal acylation or deamination;
   (b) modification of the C-terminal carboxyl group into an amide or an alcohol group;
   (c) modification at the amide bond between two amino acids by acylation or alkylation at the nitrogen atom or the alpha carbon of the amide bond linking said two amino acids;
   (d) modification at the alpha carbon of the amide bond linking two amino acids by acylation or alkylation at the alpha carbon of the amide bond linking said two amino acids;
   (e) replacement of one or more naturally occurring L-enantiomeric amino acids with a corresponding D-enantiomer;
   (f) retro-inversion, in which one or more naturally occurring L-enantiomeric amino acids is replaced with a corresponding D-enantiomer, together with inversion of the amino acid chain;
   (g) replacement of one or more alpha carbons with nitrogen atoms; and
   (h) binding of the amino group of one or more amino acid to the $\beta$ carbon instead of the $\alpha$ carbon.

\* \* \* \* \*

SEQUENCE LISTING

<160> NUMBER OF SEQ ID NOS: 101

<210> SEQ ID NO 1
<211> LENGTH: 738
<212> TYPE: PRT
<213> ORGANISM: Homo sapiens
<220> FEATURE:
<221> NAME/KEY: SIGNAL
<222> LOCATION: (1)..(27)
<220> FEATURE:
<221> NAME/KEY: DOMAIN
<222> LOCATION: (28)..(601)
<223> OTHER INFORMATION: extracellular domain
<220> FEATURE:
<221> NAME/KEY: DOMAIN
<222> LOCATION: (34)..(121)
<223> OTHER INFORMATION: First Ig-like domain
<220> FEATURE:
<221> NAME/KEY: DOMAIN
<222> LOCATION: (145)..(233)
<223> OTHER INFORMATION: Second Ig-like domain
<220> FEATURE:
<221> NAME/KEY: DOMAIN
<222> LOCATION: (236)..(315)
<223> OTHER INFORMATION: Third Ig-like domain
<220> FEATURE:
<221> NAME/KEY: DOMAIN
<222> LOCATION: (328)..(401)
<223> OTHER INFORMATION: Fourth Ig-like domain
<220> FEATURE:
<221> NAME/KEY: DOMAIN
<222> LOCATION: (424)..(493)
<223> OTHER INFORMATION: Fifth Ig-like domain
<220> FEATURE:
<221> NAME/KEY: DOMAIN
<222> LOCATION: (499)..(591)
<223> OTHER INFORMATION: Sixth Ig-like domain
<220> FEATURE:
<221> NAME/KEY: DOMAIN
<222> LOCATION: (602)..(620)
<223> OTHER INFORMATION: transmembrane domain
<220> FEATURE:
<221> NAME/KEY: DOMAIN
<222> LOCATION: (621)..(738)
<223> OTHER INFORMATION: cytoplasmic

<400> SEQUENCE: 1

Met Gln Pro Arg Trp Ala Gln Gly Ala Thr Met Trp Leu Gly Val Leu
1               5                   10                  15

Leu Thr Leu Leu Leu Cys Ser Ser Leu Glu Gly Gln Glu Asn Ser Phe
            20                  25                  30

Thr Ile Asn Ser Val Asp Met Lys Ser Leu Pro Asp Trp Thr Val Gln
        35                  40                  45

Asn Gly Lys Asn Leu Thr Leu Gln Cys Phe Ala Asp Val Ser Thr Thr
    50                  55                  60

Ser His Val Lys Pro Gln His Gln Met Leu Phe Tyr Lys Asp Asp Val
65                  70                  75                  80

Leu Phe Tyr Asn Ile Ser Ser Met Lys Ser Thr Glu Ser Tyr Phe Ile
                85                  90                  95

Pro Glu Val Arg Ile Tyr Asp Ser Gly Thr Tyr Lys Cys Thr Val Ile
            100                 105                 110

Val Asn Asn Lys Glu Lys Thr Thr Ala Glu Tyr Gln Leu Leu Val Glu
        115                 120                 125

Gly Val Pro Ser Pro Arg Val Thr Leu Asp Lys Lys Glu Ala Ile Gln
    130                 135                 140

Gly Gly Ile Val Arg Val Asn Cys Ser Val Pro Glu Glu Lys Ala Pro
145                 150                 155                 160

-continued

```
Ile His Phe Thr Ile Glu Lys Leu Glu Leu Asn Glu Lys Met Val Lys
            165                 170                 175

Leu Lys Arg Glu Lys Asn Ser Arg Asp Gln Asn Phe Val Ile Leu Glu
            180                 185                 190

Phe Pro Val Glu Glu Gln Asp Arg Val Leu Ser Phe Arg Cys Gln Ala
            195                 200                 205

Arg Ile Ile Ser Gly Ile His Met Gln Thr Ser Glu Ser Thr Lys Ser
    210                 215                 220

Glu Leu Val Thr Val Thr Glu Ser Phe Ser Thr Pro Lys Phe His Ile
225                 230                 235                 240

Ser Pro Thr Gly Met Ile Met Glu Gly Ala Gln Leu His Ile Lys Cys
                245                 250                 255

Thr Ile Gln Val Thr His Leu Ala Gln Glu Phe Pro Glu Ile Ile Ile
                260                 265                 270

Gln Lys Asp Lys Ala Ile Val Ala His Asn Arg His Gly Asn Lys Ala
        275                 280                 285

Val Tyr Ser Val Met Ala Met Val Glu His Ser Gly Asn Tyr Thr Cys
    290                 295                 300

Lys Val Glu Ser Ser Arg Ile Ser Lys Val Ser Ser Ile Val Val Asn
305                 310                 315                 320

Ile Thr Glu Leu Phe Ser Lys Pro Glu Leu Glu Ser Ser Phe Thr His
                325                 330                 335

Leu Asp Gln Gly Glu Arg Leu Asn Leu Ser Cys Ser Ile Pro Gly Ala
                340                 345                 350

Pro Pro Ala Asn Phe Thr Ile Gln Lys Glu Asp Thr Ile Val Ser Gln
            355                 360                 365

Thr Gln Asp Phe Thr Lys Ile Ala Ser Lys Ser Asp Ser Gly Thr Tyr
    370                 375                 380

Ile Cys Thr Ala Gly Ile Asp Lys Val Val Lys Ser Asn Thr Val
385                 390                 395                 400

Gln Ile Val Val Cys Glu Met Leu Ser Gln Pro Arg Ile Ser Tyr Asp
                405                 410                 415

Ala Gln Phe Glu Val Ile Lys Gly Gln Thr Ile Glu Val Arg Cys Glu
            420                 425                 430

Ser Ile Ser Gly Thr Leu Pro Ile Ser Tyr Gln Leu Leu Lys Thr Ser
    435                 440                 445

Lys Val Leu Glu Asn Ser Thr Lys Asn Ser Asn Asp Pro Ala Val Phe
    450                 455                 460

Lys Asp Asn Pro Thr Glu Asp Val Glu Tyr Gln Cys Val Ala Asp Asn
465                 470                 475                 480

Cys His Ser His Ala Lys Met Leu Ser Glu Val Leu Arg Val Lys Val
                485                 490                 495

Ile Ala Pro Val Asp Glu Val Gln Ile Ser Ile Leu Ser Ser Lys Val
                500                 505                 510

Val Glu Ser Gly Glu Asp Ile Val Leu Gln Cys Ala Val Asn Glu Gly
            515                 520                 525

Ser Gly Pro Ile Thr Tyr Lys Phe Tyr Arg Glu Lys Glu Gly Lys Pro
    530                 535                 540

Phe Tyr Gln Met Thr Ser Asn Ala Thr Gln Ala Phe Trp Thr Lys Gln
545                 550                 555                 560

Lys Ala Ser Lys Glu Gln Glu Gly Glu Tyr Tyr Cys Thr Ala Phe Asn
                565                 570                 575

Arg Ala Asn His Ala Ser Ser Val Pro Arg Ser Lys Ile Leu Thr Val
```

```
                580                 585                 590
Arg Val Ile Leu Ala Pro Trp Lys Lys Gly Leu Ile Ala Val Val Ile
            595                 600                 605

Ile Gly Val Ile Ile Ala Leu Leu Ile Ile Ala Ala Lys Cys Tyr Phe
            610                 615                 620

Leu Arg Lys Ala Lys Ala Lys Gln Met Pro Val Glu Met Ser Arg Pro
625                 630                 635                 640

Ala Val Pro Leu Leu Asn Ser Asn Asn Glu Lys Met Ser Asp Pro Asn
            645                 650                 655

Met Glu Ala Asn Ser His Tyr Gly His Asn Asp Asp Val Arg Asn His
            660                 665                 670

Ala Met Lys Pro Ile Asn Asp Asn Lys Glu Pro Leu Asn Ser Asp Val
            675                 680                 685

Gln Tyr Thr Glu Val Gln Val Ser Ser Ala Glu Ser His Lys Asp Leu
            690                 695                 700

Gly Lys Lys Asp Thr Glu Thr Val Tyr Ser Glu Val Arg Lys Ala Val
705                 710                 715                 720

Pro Asp Ala Val Glu Ser Arg Tyr Ser Arg Thr Glu Gly Ser Leu Asp
            725                 730                 735

Gly Thr

<210> SEQ ID NO 2
<211> LENGTH: 6
<212> TYPE: PRT
<213> ORGANISM: Artificial
<220> FEATURE:
<223> OTHER INFORMATION: mouse or human-derived CD31 peptide

<400> SEQUENCE: 2

Leu Ala Pro Trp Lys Lys
1               5

<210> SEQ ID NO 3
<211> LENGTH: 10
<212> TYPE: PRT
<213> ORGANISM: Artificial
<220> FEATURE:
<223> OTHER INFORMATION: mouse-derived CD31 peptide

<400> SEQUENCE: 3

Val Arg Val Phe Leu Ala Pro Trp Lys Lys
1               5                   10

<210> SEQ ID NO 4
<211> LENGTH: 10
<212> TYPE: PRT
<213> ORGANISM: Artificial
<220> FEATURE:
<223> OTHER INFORMATION: human-derived CD31 peptide

<400> SEQUENCE: 4

Val Arg Val Ile Leu Ala Pro Trp Lys Lys
1               5                   10

<210> SEQ ID NO 5
<211> LENGTH: 23
<212> TYPE: PRT
<213> ORGANISM: Artificial
<220> FEATURE:
<223> OTHER INFORMATION: mouse-derived CD31 peptide

<400> SEQUENCE: 5
```

```
Ser Ser Met Arg Thr Ser Pro Arg Ser Thr Leu Ala Val Arg Val
1               5                   10                  15

Phe Leu Ala Pro Trp Lys Lys
                20

<210> SEQ ID NO 6
<211> LENGTH: 23
<212> TYPE: PRT
<213> ORGANISM: Artificial
<220> FEATURE:
<223> OTHER INFORMATION: human-derived CD31 peptide

<400> SEQUENCE: 6

Asn His Ala Ser Ser Val Pro Arg Ser Lys Ile Leu Thr Val Arg Val
1               5                   10                  15

Ile Leu Ala Pro Trp Lys Lys
                20

<210> SEQ ID NO 7
<211> LENGTH: 727
<212> TYPE: PRT
<213> ORGANISM: Mus musculus

<400> SEQUENCE: 7

Met Leu Leu Ala Leu Gly Leu Thr Leu Val Leu Tyr Ala Ser Leu Gln
1               5                   10                  15

Ala Glu Glu Asn Ser Phe Thr Ile Asn Ser Ile His Met Glu Ser Leu
                20                  25                  30

Pro Ser Trp Glu Val Met Asn Gly Gln Gln Leu Thr Leu Glu Cys Leu
            35                  40                  45

Val Asp Ile Ser Thr Thr Ser Lys Ser Arg Ser Gln His Arg Val Leu
        50                  55                  60

Phe Tyr Lys Asp Asp Ala Met Val Tyr Asn Val Thr Ser Arg Glu His
65                  70                  75                  80

Thr Glu Ser Tyr Val Ile Pro Gln Ala Arg Val Phe His Ser Gly Lys
                85                  90                  95

Tyr Lys Cys Thr Val Met Leu Asn Asn Lys Glu Lys Thr Thr Ile Glu
            100                 105                 110

Tyr Glu Val Lys Val His Gly Val Ser Lys Pro Lys Val Thr Leu Asp
        115                 120                 125

Lys Lys Glu Val Thr Glu Gly Gly Val Val Thr Val Asn Cys Ser Leu
130                 135                 140

Gln Glu Glu Lys Pro Pro Ile Phe Phe Lys Ile Glu Lys Leu Glu Val
145                 150                 155                 160

Gly Thr Lys Phe Val Lys Arg Arg Ile Asp Lys Thr Ser Asn Glu Asn
                165                 170                 175

Phe Val Leu Met Glu Phe Pro Ile Glu Ala Gln Asp His Val Leu Val
            180                 185                 190

Phe Arg Cys Gln Ala Gly Ile Leu Ser Gly Phe Lys Leu Gln Glu Ser
        195                 200                 205

Glu Pro Ile Arg Ser Glu Tyr Val Thr Val Gln Glu Ser Phe Ser Thr
    210                 215                 220

Pro Lys Phe Glu Ile Lys Pro Pro Gly Met Ile Ile Glu Gly Asp Gln
225                 230                 235                 240

Leu His Ile Arg Cys Ile Val Gln Val Thr His Leu Val Gln Glu Phe
                245                 250                 255
```

-continued

```
Thr Glu Ile Ile Ile Gln Lys Asp Lys Ala Ile Val Ala Thr Ser Lys
            260                 265                 270
Gln Ser Ser Glu Ala Val Tyr Ser Val Met Ala Met Val Glu Tyr Ser
        275                 280                 285
Gly His Tyr Thr Cys Lys Val Glu Ser Asn Arg Ile Ser Lys Ala Ser
    290                 295                 300
Ser Ile Met Val Asn Ile Thr Glu Leu Phe Pro Lys Pro Lys Leu Glu
305                 310                 315                 320
Phe Ser Ser Ser Arg Leu Asp Gln Gly Glu Leu Leu Asp Leu Ser Cys
                325                 330                 335
Ser Val Ser Gly Thr Pro Val Ala Asn Phe Thr Ile Gln Lys Glu Glu
            340                 345                 350
Thr Val Leu Ser Gln Tyr Gln Asn Phe Ser Lys Ile Ala Glu Glu Ser
        355                 360                 365
Asp Ser Gly Glu Tyr Ser Cys Thr Ala Gly Ile Gly Lys Val Val Lys
    370                 375                 380
Arg Ser Gly Leu Val Pro Ile Gln Val Cys Glu Met Leu Ser Lys Pro
385                 390                 395                 400
Ser Ile Phe His Asp Ala Lys Ser Glu Ile Ile Lys Gly His Ala Ile
                405                 410                 415
Gly Ile Ser Cys Gln Ser Glu Asn Gly Thr Ala Pro Ile Thr Tyr His
            420                 425                 430
Leu Met Lys Ala Lys Ser Asp Phe Gln Thr Leu Glu Val Thr Ser Asn
        435                 440                 445
Asp Pro Ala Thr Phe Thr Asp Lys Pro Thr Arg Asp Met Glu Tyr Gln
    450                 455                 460
Cys Arg Ala Asp Asn Cys His Ser His Pro Ala Val Phe Ser Glu Ile
465                 470                 475                 480
Leu Arg Val Arg Val Ile Ala Pro Val Asp Glu Val Val Ile Ser Ile
                485                 490                 495
Leu Ser Ser Asn Glu Val Gln Ser Gly Ser Glu Met Val Leu Arg Cys
            500                 505                 510
Ser Val Lys Glu Gly Thr Ser Pro Ile Thr Phe Gln Phe Tyr Lys Glu
        515                 520                 525
Lys Glu Asp Arg Pro Phe His Gln Ala Val Val Asn Asp Thr Gln Ala
    530                 535                 540
Phe Trp His Asn Lys Gln Ala Ser Lys Lys Gln Glu Gly Gln Tyr Tyr
545                 550                 555                 560
Cys Thr Ala Ser Asn Arg Ala Ser Ser Met Arg Thr Ser Pro Arg Ser
                565                 570                 575
Ser Thr Leu Ala Val Arg Val Phe Leu Ala Pro Trp Lys Lys Gly Leu
            580                 585                 590
Ile Ala Val Val Val Ile Gly Val Val Ile Ala Thr Leu Ile Val Ala
        595                 600                 605
Ala Lys Cys Tyr Phe Leu Arg Lys Ala Lys Ala Lys Gln Lys Pro Val
    610                 615                 620
Glu Met Ser Arg Pro Ala Ala Pro Leu Leu Asn Ser Asn Ser Glu Lys
625                 630                 635                 640
Ile Ser Glu Pro Ser Val Glu Ala Asn Ser His Tyr Gly Tyr Asp Asp
                645                 650                 655
Val Ser Gly Asn Asp Ala Val Lys Pro Ile Asn Gln Asn Lys Asp Pro
            660                 665                 670
Gln Asn Met Asp Val Glu Tyr Thr Glu Val Glu Val Ser Ser Leu Glu
```

675                 680                 685
Pro His Gln Ala Leu Gly Thr Arg Ala Thr Glu Thr Val Tyr Ser Glu
        690                 695                 700

Ile Arg Lys Val Asp Pro Asn Leu Met Glu Asn Arg Tyr Ser Arg Thr
705                 710                 715                 720

Glu Gly Ser Leu Asn Gly Thr
                725

<210> SEQ ID NO 8
<211> LENGTH: 739
<212> TYPE: PRT
<213> ORGANISM: Bos taurus

<400> SEQUENCE: 8

Met Gln Leu Arg Trp Thr Gln Arg Gly Met Met Trp Leu Gly Ala Leu
1               5                   10                  15

Leu Thr Leu Leu Leu Cys Ser Ser Leu Lys Gly Gln Glu Asn Ser Phe
            20                  25                  30

Thr Ile Asn Ser Ile His Met Gln Ile Leu Pro His Ser Thr Val Gln
        35                  40                  45

Asn Gly Glu Asn Leu Thr Leu Gln Cys Leu Val Asp Val Ser Thr Thr
    50                  55                  60

Ser Arg Val Lys Pro Leu His Gln Val Leu Phe Tyr Lys Asp Asp Val
65                  70                  75                  80

Leu Leu His Asn Val Ser Ser Arg Arg Asn Thr Glu Ser Tyr Leu Ile
                85                  90                  95

Pro His Val Arg Val Cys Asp Ser Gly Arg Tyr Lys Cys Asn Val Ile
            100                 105                 110

Leu Asn Asn Lys Glu Lys Thr Thr Pro Glu Tyr Glu Val Trp Val Lys
        115                 120                 125

Gly Val Ser Asp Pro Arg Val Thr Leu Asp Lys Lys Glu Val Ile Glu
    130                 135                 140

Gly Gly Val Val Val Asn Cys Ser Val Pro Glu Glu Lys Ala Pro
145                 150                 155                 160

Val His Phe Thr Ile Glu Lys Phe Glu Leu Asn Ile Arg Gly Ala Lys
                165                 170                 175

Lys Lys Arg Glu Lys Thr Ser Gln Asn Gln Asn Phe Val Thr Leu Glu
            180                 185                 190

Phe Thr Val Glu Glu Gln Asp Arg Thr Ile Arg Phe Gln Cys Gln Ala
        195                 200                 205

Lys Ile Phe Ser Gly Ser Asn Val Glu Ser Ser Arg Pro Ile Gln Ser
    210                 215                 220

Asp Leu Val Thr Val Arg Glu Ser Phe Ser Asn Pro Lys Phe His Ile
225                 230                 235                 240

Ile Pro Glu Gly Lys Val Met Glu Gly Asp Asp Leu Gln Val Lys Cys
                245                 250                 255

Thr Val Gln Val Thr His Gln Ala Gln Ser Phe Pro Glu Ile Ile Ile
            260                 265                 270

Gln Lys Asp Arg Glu Ile Val Ala His Asn Ser Leu Ser Ser Glu Ala
        275                 280                 285

Val Tyr Ser Val Met Ala Thr Thr Glu His Asn Gly Asn Tyr Thr Cys
    290                 295                 300

Lys Val Glu Ala Ser Arg Ile Ser Lys Val Ser Ser Val Val Val Asn
305                 310                 315                 320

-continued

```
Val Thr Glu Leu Phe Ser Lys Pro Lys Leu Glu Ser Ala Thr His
            325                 330                 335

Leu Asp Gln Gly Glu Asp Leu Asn Leu Leu Cys Ser Ile Pro Gly Ala
            340                 345                 350

Pro Pro Ala Asn Phe Thr Ile Gln Lys Gly Gly Met Thr Val Ser Gln
            355                 360                 365

Thr Gln Asn Phe Thr Lys Arg Val Ser Glu Trp Asp Ser Gly Leu Tyr
    370                 375                 380

Thr Cys Val Ala Gly Val Gly Arg Val Phe Lys Arg Ser Asn Thr Val
385                 390                 395                 400

Gln Ile Thr Val Cys Glu Met Leu Ser Lys Pro Ser Ile Phe His Asp
            405                 410                 415

Ser Arg Ser Glu Val Ile Lys Gly Gln Thr Ile Glu Val Ser Cys Gln
            420                 425                 430

Ser Val Asn Gly Thr Ala Pro Ile Phe Tyr Gln Leu Ser Asn Thr Ser
            435                 440                 445

Lys Pro Val Ala Asn Gln Ser Val Gly Ser Asn Lys Pro Ala Ile Phe
    450                 455                 460

Arg Val Lys Pro Thr Lys Asp Val Glu Tyr Cys Cys Ser Ala Asp Asn
465                 470                 475                 480

Cys His Ser His Ser Lys Met Phe Ser Glu Val Leu Arg Val Lys Val
            485                 490                 495

Ile Ala Pro Val Asp Glu Ala Gln Leu Val Val Leu Lys Gly Glu Val
            500                 505                 510

Glu Pro Gly Glu Pro Ile Val Phe Tyr Cys Ser Val Asn Glu Gly Ser
            515                 520                 525

Phe Pro Ile Thr Tyr Lys Phe Tyr Lys Glu Lys Glu Ser Lys Pro Phe
    530                 535                 540

Tyr Gln Asp Thr Ile Asn Ala Thr Gln Ile Met Trp His Lys Thr Thr
545                 550                 555                 560

Ala Ser Lys Glu Tyr Glu Gly Gln Tyr Tyr Cys Thr Ala Ser Asn Arg
            565                 570                 575

Ala Asn Leu Ser Lys His Val Ile Gln Ser Asn Thr Leu Thr Val Arg
            580                 585                 590

Val Tyr Leu Pro Leu Glu Lys Gly Leu Ile Ala Val Val Ile Gly
            595                 600                 605

Val Ile Ile Val Thr Leu Val Leu Gly Ala Lys Cys Tyr Phe Leu Lys
    610                 615                 620

Lys Ala Lys Ala Lys Gln Met Pro Val Glu Met Ser Arg Pro Ala Val
625                 630                 635                 640

Pro Leu Leu Asn Ser Asn Asn Glu Lys Thr Leu Ser Asp Ala Gly Thr
            645                 650                 655

Glu Ala Asp Arg His Tyr Gly Tyr Asn Glu Asp Val Gly Asn His Ala
            660                 665                 670

Met Lys Pro Leu Asn Glu Asn Lys Glu Pro Leu Thr Leu Asp Val Glu
            675                 680                 685

Tyr Thr Glu Val Glu Val Thr Ser Pro Glu Pro His Gln Gly Leu Gly
            690                 695                 700

Thr Lys Gly Thr Glu Thr Glu Thr Val Tyr Ser Glu Ile Arg Lys Ala
705                 710                 715                 720

Asp Pro Asp Phe Val Glu Asn Arg Tyr Ser Arg Thr Glu Gly Ser Leu
            725                 730                 735

Asp Gly Ser
```

<210> SEQ ID NO 9
<211> LENGTH: 740
<212> TYPE: PRT
<213> ORGANISM: Sus scrofa

<400> SEQUENCE: 9

```
Met Arg Leu Arg Trp Thr Gln Gly Gly Asn Met Trp Leu Gly Val Leu
1               5                   10                  15

Leu Thr Leu Gln Leu Cys Ser Ser Leu Glu Gly Gln Glu Asn Ser Phe
            20                  25                  30

Thr Ile Asn Ser Ile His Met Glu Met Leu Pro Gly Gln Glu Val His
        35                  40                  45

Asn Gly Glu Asn Leu Thr Leu Gln Cys Ile Val Asp Val Ser Thr Thr
    50                  55                  60

Ser Ser Val Lys Pro Gln His Gln Val Leu Phe Tyr Lys Asp Asp Val
65                  70                  75                  80

Leu Phe His Asn Val Ser Ser Thr Lys Asn Thr Glu Ser Tyr Phe Ile
                85                  90                  95

Ser Glu Ala Arg Val Tyr Asn Ser Gly Arg Tyr Lys Cys Thr Val Ile
            100                 105                 110

Leu Asn Asn Lys Glu Lys Thr Thr Ala Glu Tyr Lys Val Val Val Glu
        115                 120                 125

Gly Val Ser Asn Pro Arg Val Thr Leu Asp Lys Lys Glu Val Ile Glu
    130                 135                 140

Gly Gly Val Val Lys Val Thr Cys Ser Val Pro Glu Glu Lys Pro Pro
145                 150                 155                 160

Val His Phe Ile Ile Glu Lys Phe Glu Leu Asn Val Arg Asp Val Lys
                165                 170                 175

Gln Arg Arg Glu Lys Thr Ala Asn Asn Gln Asn Ser Val Thr Leu Glu
            180                 185                 190

Phe Thr Val Glu Glu Gln Asp Arg Val Ile Leu Phe Ser Cys Gln Ala
        195                 200                 205

Asn Val Ile Phe Gly Thr Arg Val Glu Ile Ser Asp Ser Val Arg Ser
    210                 215                 220

Asp Leu Val Thr Val Arg Glu Ser Phe Ser Asn Pro Lys Phe His Ile
225                 230                 235                 240

Ser Pro Lys Gly Val Ile Ile Glu Gly Asp Gln Leu Leu Ile Lys Cys
                245                 250                 255

Thr Ile Gln Val Thr His Gln Ala Gln Ser Phe Pro Glu Ile Ile Ile
            260                 265                 270

Gln Lys Asp Lys Glu Ile Val Ala His Ser Arg Asn Gly Ser Glu Ala
        275                 280                 285

Val Tyr Ser Val Met Ala Thr Val Glu His Asn Ser Asn Tyr Thr Cys
    290                 295                 300

Lys Val Glu Ala Ser Arg Ile Ser Lys Val Ser Ser Ile Met Val Asn
305                 310                 315                 320

Ile Thr Glu Leu Phe Ser Arg Pro Lys Leu Lys Ser Ser Ala Thr Arg
                325                 330                 335

Leu Asp Gln Gly Glu Ser Leu Arg Leu Trp Cys Ser Ile Pro Gly Ala
            340                 345                 350

Pro Pro Glu Ala Asn Phe Thr Ile Gln Lys Gly Gly Met Met Met Leu
        355                 360                 365

Gln Asp Gln Asn Leu Thr Lys Val Ala Ser Glu Arg Asp Ser Gly Thr
```

```
                370             375             380
Tyr Thr Cys Val Ala Gly Ile Gly Lys Val Val Lys Arg Ser Asn Glu
385                 390             395                 400

Val Gln Ile Ala Val Cys Glu Met Leu Ser Lys Pro Ser Ile Phe His
                405             410                 415

Asp Ser Gly Ser Glu Val Ile Lys Gly Gln Thr Ile Glu Val Ser Cys
            420             425                 430

Gln Ser Ile Asn Gly Thr Ser Pro Ile Ser Tyr Gln Leu Leu Lys Gly
            435             440                 445

Ser Asp Leu Leu Ala Ser Gln Asn Val Ser Ser Asn Glu Pro Ala Val
    450             455             460

Phe Lys Asp Asn Pro Thr Lys Asp Val Glu Tyr Gln Cys Ile Ala Asp
465             470             475                 480

Asn Cys His Ser His Ala Gly Met Pro Ser Lys Val Leu Arg Val Lys
                485             490                 495

Val Ile Ala Pro Val Glu Glu Val Lys Leu Ser Ile Leu Leu Ser Glu
            500             505             510

Glu Val Glu Ser Gly Gln Ala Ile Val Leu Gln Cys Ser Val Lys Glu
    515             520             525

Gly Ser Gly Pro Ile Thr Tyr Lys Phe Tyr Lys Glu Lys Glu Asn Lys
530             535             540

Pro Phe His Gln Val Thr Leu Asn Asp Thr Gln Ala Ile Trp His Lys
545             550             555                 560

Pro Lys Ala Ser Lys Asp Gln Glu Gly Gln Tyr Tyr Cys Leu Ala Ser
                565             570                 575

Asn Arg Ala Thr Pro Ser Lys Asn Phe Leu Gln Ser Asn Ile Leu Ala
            580             585             590

Val Arg Val Tyr Leu Ala Pro Trp Lys Lys Gly Leu Ile Ala Val Val
            595             600             605

Val Ile Ala Val Ile Ile Ala Val Leu Leu Leu Gly Ala Arg Phe Tyr
    610             615             620

Phe Leu Lys Lys Ser Lys Ala Lys Gln Met Pro Val Glu Met Cys Arg
625             630             635             640

Pro Ala Ala Pro Leu Leu Asn Ser Asn Asn Glu Lys Thr Leu Ser Asp
                645             650             655

Pro Asn Thr Glu Ala Asn Arg His Tyr Gly Tyr Asn Glu Asp Val Gly
            660             665             670

Asn His Ala Met Lys Pro Leu Asn Glu Asn Lys Glu Pro Leu Thr Leu
            675             680             685

Asp Val Glu Tyr Thr Glu Val Glu Val Thr Ser Pro Glu Pro His Arg
    690             695             700

Gly Leu Gly Thr Lys Gly Thr Glu Thr Val Tyr Ser Glu Ile Arg Lys
705             710             715                 720

Ala Asp Pro Asp Leu Val Glu Asn Arg Tyr Ser Arg Thr Glu Gly Ser
                725             730             735

Leu Asp Gly Thr
            740

<210> SEQ ID NO 10
<211> LENGTH: 10
<212> TYPE: PRT
<213> ORGANISM: Artificial
<220> FEATURE:
<223> OTHER INFORMATION: rat-derived CD31 peptide
```

```
<400> SEQUENCE: 10

Val Arg Val Phe Leu Ala Pro Trp Lys Lys
1               5                   10

<210> SEQ ID NO 11
<211> LENGTH: 10
<212> TYPE: PRT
<213> ORGANISM: Artificial
<220> FEATURE:
<223> OTHER INFORMATION: pig-derived CD31 peptide

<400> SEQUENCE: 11

Val Arg Val Tyr Leu Ala Pro Trp Lys Lys
1               5                   10

<210> SEQ ID NO 12
<211> LENGTH: 9
<212> TYPE: PRT
<213> ORGANISM: Artificial
<220> FEATURE:
<223> OTHER INFORMATION: bovin-derived CD31 peptide

<400> SEQUENCE: 12

Val Arg Val Tyr Leu Pro Leu Glu Lys
1               5

<210> SEQ ID NO 13
<211> LENGTH: 23
<212> TYPE: PRT
<213> ORGANISM: Artificial
<220> FEATURE:
<223> OTHER INFORMATION: scramble peptide

<400> SEQUENCE: 13

Ser Met Pro Ala Val Arg Ser Arg Phe Ser Ala Thr Ser Leu Val Thr
1               5                   10                  15

Leu Lys Ser Arg Trp Pro Lys
            20

<210> SEQ ID NO 14
<211> LENGTH: 10
<212> TYPE: PRT
<213> ORGANISM: Artificial
<220> FEATURE:
<223> OTHER INFORMATION: scramble peptide

<400> SEQUENCE: 14

Trp Pro Lys Leu Arg Lys Phe Val Ala Val
1               5                   10

<210> SEQ ID NO 15
<211> LENGTH: 22
<212> TYPE: PRT
<213> ORGANISM: Artificial Sequence
<220> FEATURE:
<223> OTHER INFORMATION: CD31 peptide

<400> SEQUENCE: 15

Ser Met Arg Thr Ser Pro Arg Ser Ser Thr Leu Ala Val Arg Val Phe
1               5                   10                  15

Leu Ala Pro Trp Lys Lys
            20

<210> SEQ ID NO 16
<211> LENGTH: 21
```

```
<212> TYPE: PRT
<213> ORGANISM: Artificial Sequence
<220> FEATURE:
<223> OTHER INFORMATION: CD31 peptide

<400> SEQUENCE: 16

Met Arg Thr Ser Pro Arg Ser Ser Thr Leu Ala Val Arg Val Phe Leu
1               5                   10                  15

Ala Pro Trp Lys Lys
            20

<210> SEQ ID NO 17
<211> LENGTH: 20
<212> TYPE: PRT
<213> ORGANISM: Artificial Sequence
<220> FEATURE:
<223> OTHER INFORMATION: CD31 peptide

<400> SEQUENCE: 17

Arg Thr Ser Pro Arg Ser Ser Thr Leu Ala Val Arg Val Phe Leu Ala
1               5                   10                  15

Pro Trp Lys Lys
            20

<210> SEQ ID NO 18
<211> LENGTH: 19
<212> TYPE: PRT
<213> ORGANISM: Artificial Sequence
<220> FEATURE:
<223> OTHER INFORMATION: CD31 peptide

<400> SEQUENCE: 18

Thr Ser Pro Arg Ser Ser Thr Leu Ala Val Arg Val Phe Leu Ala Pro
1               5                   10                  15

Trp Lys Lys

<210> SEQ ID NO 19
<211> LENGTH: 18
<212> TYPE: PRT
<213> ORGANISM: Artificial Sequence
<220> FEATURE:
<223> OTHER INFORMATION: CD31 peptide

<400> SEQUENCE: 19

Ser Pro Arg Ser Ser Thr Leu Ala Val Arg Val Phe Leu Ala Pro Trp
1               5                   10                  15

Lys Lys

<210> SEQ ID NO 20
<211> LENGTH: 17
<212> TYPE: PRT
<213> ORGANISM: Artificial Sequence
<220> FEATURE:
<223> OTHER INFORMATION: CD31 peptide

<400> SEQUENCE: 20

Pro Arg Ser Ser Thr Leu Ala Val Arg Val Phe Leu Ala Pro Trp Lys
1               5                   10                  15

Lys

<210> SEQ ID NO 21
<211> LENGTH: 16
<212> TYPE: PRT
<213> ORGANISM: Artificial Sequence
```

```
<220> FEATURE:
<223> OTHER INFORMATION: CD31 peptide

<400> SEQUENCE: 21

Arg Ser Ser Thr Leu Ala Val Arg Val Phe Leu Ala Pro Trp Lys Lys
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: CD31 peptide

<400> SEQUENCE: 22

Ser Ser Thr Leu Ala Val Arg Val Phe Leu Ala Pro Trp Lys Lys
1               5                   10                  15

<210> SEQ ID NO 23
<211> LENGTH: 14
<212> TYPE: PRT
<213> ORGANISM: Artificial Sequence
<220> FEATURE:
<223> OTHER INFORMATION: CD31 peptide

<400> SEQUENCE: 23

Ser Thr Leu Ala Val Arg Val Phe Leu Ala Pro Trp Lys Lys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: CD31 peptide

<400> SEQUENCE: 24

Thr Leu Ala Val Arg Val Phe Leu Ala Pro Trp Lys Lys
1               5                   10

<210> SEQ ID NO 25
<211> LENGTH: 12
<212> TYPE: PRT
<213> ORGANISM: Artificial Sequence
<220> FEATURE:
<223> OTHER INFORMATION: CD31 peptide

<400> SEQUENCE: 25

Leu Ala Val Arg Val Phe Leu Ala Pro Trp Lys Lys
1               5                   10

<210> SEQ ID NO 26
<211> LENGTH: 11
<212> TYPE: PRT
<213> ORGANISM: Artificial Sequence
<220> FEATURE:
<223> OTHER INFORMATION: CD31 peptide

<400> SEQUENCE: 26

Ala Val Arg Val Phe Leu Ala Pro Trp Lys Lys
1               5                   10

<210> SEQ ID NO 27
<211> LENGTH: 9
<212> TYPE: PRT
<213> ORGANISM: Artificial Sequence
<220> FEATURE:
```

```
<223> OTHER INFORMATION: CD31 peptide

<400> SEQUENCE: 27

Arg Val Phe Leu Ala Pro Trp Lys Lys
1               5

<210> SEQ ID NO 28
<211> LENGTH: 8
<212> TYPE: PRT
<213> ORGANISM: Artificial Sequence
<220> FEATURE:
<223> OTHER INFORMATION: CD31 peptide

<400> SEQUENCE: 28

Val Phe Leu Ala Pro Trp Lys Lys
1               5

<210> SEQ ID NO 29
<211> LENGTH: 7
<212> TYPE: PRT
<213> ORGANISM: Artificial Sequence
<220> FEATURE:
<223> OTHER INFORMATION: CD31 peptide

<400> SEQUENCE: 29

Phe Leu Ala Pro Trp Lys Lys
1               5

<210> SEQ ID NO 30
<211> LENGTH: 5
<212> TYPE: PRT
<213> ORGANISM: Artificial Sequence
<220> FEATURE:
<223> OTHER INFORMATION: CD31 peptide

<400> SEQUENCE: 30

Ala Pro Trp Lys Lys
1               5

<210> SEQ ID NO 31
<211> LENGTH: 4
<212> TYPE: PRT
<213> ORGANISM: Artificial Sequence
<220> FEATURE:
<223> OTHER INFORMATION: CD31 peptide

<400> SEQUENCE: 31

Pro Trp Lys Lys
1

<210> SEQ ID NO 32
<211> LENGTH: 22
<212> TYPE: PRT
<213> ORGANISM: Artificial Sequence
<220> FEATURE:
<223> OTHER INFORMATION: CD31 peptide

<400> SEQUENCE: 32

His Ala Ser Ser Val Pro Arg Ser Lys Ile Leu Thr Val Arg Val Ile
1               5                   10                  15

Leu Ala Pro Trp Lys Lys
            20

<210> SEQ ID NO 33
<211> LENGTH: 21
<212> TYPE: PRT
```

```
<213> ORGANISM: Artificial Sequence
<220> FEATURE:
<223> OTHER INFORMATION: CD31 peptide

<400> SEQUENCE: 33

Ala Ser Ser Val Pro Arg Ser Lys Ile Leu Thr Val Arg Val Ile Leu
1               5                   10                  15

Ala Pro Trp Lys Lys
            20

<210> SEQ ID NO 34
<211> LENGTH: 20
<212> TYPE: PRT
<213> ORGANISM: Artificial Sequence
<220> FEATURE:
<223> OTHER INFORMATION: CD31 peptide

<400> SEQUENCE: 34

Ser Ser Val Pro Arg Ser Lys Ile Leu Thr Val Arg Val Ile Leu Ala
1               5                   10                  15

Pro Trp Lys Lys
            20

<210> SEQ ID NO 35
<211> LENGTH: 19
<212> TYPE: PRT
<213> ORGANISM: Artificial Sequence
<220> FEATURE:
<223> OTHER INFORMATION: CD31 peptide

<400> SEQUENCE: 35

Ser Val Pro Arg Ser Lys Ile Leu Thr Val Arg Val Ile Leu Ala Pro
1               5                   10                  15

Trp Lys Lys

<210> SEQ ID NO 36
<211> LENGTH: 18
<212> TYPE: PRT
<213> ORGANISM: Artificial Sequence
<220> FEATURE:
<223> OTHER INFORMATION: CD31 peptide

<400> SEQUENCE: 36

Val Pro Arg Ser Lys Ile Leu Thr Val Arg Val Ile Leu Ala Pro Trp
1               5                   10                  15

Lys Lys

<210> SEQ ID NO 37
<211> LENGTH: 17
<212> TYPE: PRT
<213> ORGANISM: Artificial Sequence
<220> FEATURE:
<223> OTHER INFORMATION: CD31 peptide

<400> SEQUENCE: 37

Pro Arg Ser Lys Ile Leu Thr Val Arg Val Ile Leu Ala Pro Trp Lys
1               5                   10                  15

Lys

<210> SEQ ID NO 38
<211> LENGTH: 16
<212> TYPE: PRT
<213> ORGANISM: Artificial Sequence
<220> FEATURE:
```

<223> OTHER INFORMATION: CD31 peptide

<400> SEQUENCE: 38

Arg Ser Lys Ile Leu Thr Val Arg Val Ile Leu Ala Pro Trp Lys Lys
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: CD31 peptide

<400> SEQUENCE: 39

Ser Lys Ile Leu Thr Val Arg Val Ile Leu Ala Pro Trp Lys Lys
1               5                   10                  15

<210> SEQ ID NO 40
<211> LENGTH: 14
<212> TYPE: PRT
<213> ORGANISM: Artificial Sequence
<220> FEATURE:
<223> OTHER INFORMATION: CD31 peptide

<400> SEQUENCE: 40

Lys Ile Leu Thr Val Arg Val Ile Leu Ala Pro Trp Lys Lys
1               5                   10

<210> SEQ ID NO 41
<211> LENGTH: 13
<212> TYPE: PRT
<213> ORGANISM: Artificial Sequence
<220> FEATURE:
<223> OTHER INFORMATION: CD31 peptide

<400> SEQUENCE: 41

Ile Leu Thr Val Arg Val Ile Leu Ala Pro Trp Lys Lys
1               5                   10

<210> SEQ ID NO 42
<211> LENGTH: 12
<212> TYPE: PRT
<213> ORGANISM: Artificial Sequence
<220> FEATURE:
<223> OTHER INFORMATION: CD31 peptide

<400> SEQUENCE: 42

Leu Thr Val Arg Val Ile Leu Ala Pro Trp Lys Lys
1               5                   10

<210> SEQ ID NO 43
<211> LENGTH: 11
<212> TYPE: PRT
<213> ORGANISM: Artificial Sequence
<220> FEATURE:
<223> OTHER INFORMATION: CD31 peptide

<400> SEQUENCE: 43

Thr Val Arg Val Ile Leu Ala Pro Trp Lys Lys
1               5                   10

<210> SEQ ID NO 44
<211> LENGTH: 9
<212> TYPE: PRT
<213> ORGANISM: Artificial Sequence
<220> FEATURE:
<223> OTHER INFORMATION: CD31 peptide

```
<400> SEQUENCE: 44

Arg Val Ile Leu Ala Pro Trp Lys Lys
1               5

<210> SEQ ID NO 45
<211> LENGTH: 8
<212> TYPE: PRT
<213> ORGANISM: Artificial Sequence
<220> FEATURE:
<223> OTHER INFORMATION: CD31 peptide

<400> SEQUENCE: 45

Val Ile Leu Ala Pro Trp Lys Lys
1               5

<210> SEQ ID NO 46
<211> LENGTH: 7
<212> TYPE: PRT
<213> ORGANISM: Artificial Sequence
<220> FEATURE:
<223> OTHER INFORMATION: CD31 peptide

<400> SEQUENCE: 46

Ile Leu Ala Pro Trp Lys Lys
1               5

<210> SEQ ID NO 47
<211> LENGTH: 22
<212> TYPE: PRT
<213> ORGANISM: Artificial Sequence
<220> FEATURE:
<223> OTHER INFORMATION: CD31 peptide

<400> SEQUENCE: 47

Ser Ser Met Arg Thr Ser Pro Arg Ser Ser Thr Leu Ala Val Arg Val
1               5                   10                  15

Phe Leu Ala Pro Trp Lys
            20

<210> SEQ ID NO 48
<211> LENGTH: 21
<212> TYPE: PRT
<213> ORGANISM: Artificial Sequence
<220> FEATURE:
<223> OTHER INFORMATION: CD31 peptide

<400> SEQUENCE: 48

Ser Ser Met Arg Thr Ser Pro Arg Ser Ser Thr Leu Ala Val Arg Val
1               5                   10                  15

Phe Leu Ala Pro Trp
            20

<210> SEQ ID NO 49
<211> LENGTH: 20
<212> TYPE: PRT
<213> ORGANISM: Artificial Sequence
<220> FEATURE:
<223> OTHER INFORMATION: CD31 peptide

<400> SEQUENCE: 49

Ser Ser Met Arg Thr Ser Pro Arg Ser Ser Thr Leu Ala Val Arg Val
1               5                   10                  15

Phe Leu Ala Pro
            20
```

```
<210> SEQ ID NO 50
<211> LENGTH: 19
<212> TYPE: PRT
<213> ORGANISM: Artificial Sequence
<220> FEATURE:
<223> OTHER INFORMATION: CD31 peptide

<400> SEQUENCE: 50

Ser Ser Met Arg Thr Ser Pro Arg Ser Ser Thr Leu Ala Val Arg Val
1               5                   10                  15

Phe Leu Ala

<210> SEQ ID NO 51
<211> LENGTH: 18
<212> TYPE: PRT
<213> ORGANISM: Artificial Sequence
<220> FEATURE:
<223> OTHER INFORMATION: CD31 peptide

<400> SEQUENCE: 51

Ser Ser Met Arg Thr Ser Pro Arg Ser Ser Thr Leu Ala Val Arg Val
1               5                   10                  15

Phe Leu

<210> SEQ ID NO 52
<211> LENGTH: 17
<212> TYPE: PRT
<213> ORGANISM: Artificial Sequence
<220> FEATURE:
<223> OTHER INFORMATION: CD31 peptide

<400> SEQUENCE: 52

Ser Ser Met Arg Thr Ser Pro Arg Ser Ser Thr Leu Ala Val Arg Val
1               5                   10                  15

Phe

<210> SEQ ID NO 53
<211> LENGTH: 15
<212> TYPE: PRT
<213> ORGANISM: Artificial Sequence
<220> FEATURE:
<223> OTHER INFORMATION: CD31 peptide

<400> SEQUENCE: 53

Ser Ser Met Arg Thr Ser Pro Arg Ser Ser Thr Leu Ala Val Arg
1               5                   10                  15

<210> SEQ ID NO 54
<211> LENGTH: 14
<212> TYPE: PRT
<213> ORGANISM: Artificial Sequence
<220> FEATURE:
<223> OTHER INFORMATION: CD31 peptide

<400> SEQUENCE: 54

Ser Ser Met Arg Thr Ser Pro Arg Ser Ser Thr Leu Ala Val
1               5                   10

<210> SEQ ID NO 55
<211> LENGTH: 13
<212> TYPE: PRT
<213> ORGANISM: Artificial Sequence
<220> FEATURE:
<223> OTHER INFORMATION: CD31 peptide
```

```
<400> SEQUENCE: 55

Ser Ser Met Arg Thr Ser Pro Arg Ser Ser Thr Leu Ala
1               5                   10

<210> SEQ ID NO 56
<211> LENGTH: 12
<212> TYPE: PRT
<213> ORGANISM: Artificial Sequence
<220> FEATURE:
<223> OTHER INFORMATION: CD31 peptide

<400> SEQUENCE: 56

Ser Ser Met Arg Thr Ser Pro Arg Ser Ser Thr Leu
1               5                   10

<210> SEQ ID NO 57
<211> LENGTH: 11
<212> TYPE: PRT
<213> ORGANISM: Artificial Sequence
<220> FEATURE:
<223> OTHER INFORMATION: CD31 peptide

<400> SEQUENCE: 57

Ser Ser Met Arg Thr Ser Pro Arg Ser Ser Thr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: CD31 peptide

<400> SEQUENCE: 58

Ser Ser Met Arg Thr Ser Pro Arg Ser Ser
1               5                   10

<210> SEQ ID NO 59
<211> LENGTH: 9
<212> TYPE: PRT
<213> ORGANISM: Artificial Sequence
<220> FEATURE:
<223> OTHER INFORMATION: CD31 peptide

<400> SEQUENCE: 59

Ser Ser Met Arg Thr Ser Pro Arg Ser
1               5

<210> SEQ ID NO 60
<211> LENGTH: 8
<212> TYPE: PRT
<213> ORGANISM: Artificial Sequence
<220> FEATURE:
<223> OTHER INFORMATION: CD31 peptide

<400> SEQUENCE: 60

Ser Ser Met Arg Thr Ser Pro Arg
1               5

<210> SEQ ID NO 61
<211> LENGTH: 7
<212> TYPE: PRT
<213> ORGANISM: Artificial Sequence
<220> FEATURE:
<223> OTHER INFORMATION: CD31 peptide
```

```
<400> SEQUENCE: 61

Ser Ser Met Arg Thr Ser Pro
1               5

<210> SEQ ID NO 62
<211> LENGTH: 6
<212> TYPE: PRT
<213> ORGANISM: Artificial Sequence
<220> FEATURE:
<223> OTHER INFORMATION: CD31 peptide

<400> SEQUENCE: 62

Ser Ser Met Arg Thr Ser
1               5

<210> SEQ ID NO 63
<211> LENGTH: 5
<212> TYPE: PRT
<213> ORGANISM: Artificial Sequence
<220> FEATURE:
<223> OTHER INFORMATION: CD31 peptide

<400> SEQUENCE: 63

Ser Ser Met Arg Thr
1               5

<210> SEQ ID NO 64
<211> LENGTH: 4
<212> TYPE: PRT
<213> ORGANISM: Artificial Sequence
<220> FEATURE:
<223> OTHER INFORMATION: CD31 peptide

<400> SEQUENCE: 64

Ser Ser Met Arg
1

<210> SEQ ID NO 65
<211> LENGTH: 22
<212> TYPE: PRT
<213> ORGANISM: Artificial Sequence
<220> FEATURE:
<223> OTHER INFORMATION: CD31 peptide

<400> SEQUENCE: 65

Asn His Ala Ser Ser Val Pro Arg Ser Lys Ile Leu Thr Val Arg Val
1               5                   10                  15

Ile Leu Ala Pro Trp Lys
            20

<210> SEQ ID NO 66
<211> LENGTH: 21
<212> TYPE: PRT
<213> ORGANISM: Artificial Sequence
<220> FEATURE:
<223> OTHER INFORMATION: CD31 peptide

<400> SEQUENCE: 66

Asn His Ala Ser Ser Val Pro Arg Ser Lys Ile Leu Thr Val Arg Val
1               5                   10                  15

Ile Leu Ala Pro Trp
            20

<210> SEQ ID NO 67
<211> LENGTH: 20
```

```
<212> TYPE: PRT
<213> ORGANISM: Artificial Sequence
<220> FEATURE:
<223> OTHER INFORMATION: CD31 peptide

<400> SEQUENCE: 67

Asn His Ala Ser Ser Val Pro Arg Ser Lys Ile Leu Thr Val Arg Val
1               5                   10                  15

Ile Leu Ala Pro
            20

<210> SEQ ID NO 68
<211> LENGTH: 19
<212> TYPE: PRT
<213> ORGANISM: Artificial Sequence
<220> FEATURE:
<223> OTHER INFORMATION: CD31 peptide

<400> SEQUENCE: 68

Asn His Ala Ser Ser Val Pro Arg Ser Lys Ile Leu Thr Val Arg Val
1               5                   10                  15

Ile Leu Ala

<210> SEQ ID NO 69
<211> LENGTH: 18
<212> TYPE: PRT
<213> ORGANISM: Artificial Sequence
<220> FEATURE:
<223> OTHER INFORMATION: CD31 peptide

<400> SEQUENCE: 69

Asn His Ala Ser Ser Val Pro Arg Ser Lys Ile Leu Thr Val Arg Val
1               5                   10                  15

Ile Leu

<210> SEQ ID NO 70
<211> LENGTH: 17
<212> TYPE: PRT
<213> ORGANISM: Artificial Sequence
<220> FEATURE:
<223> OTHER INFORMATION: CD31 peptide

<400> SEQUENCE: 70

Asn His Ala Ser Ser Val Pro Arg Ser Lys Ile Leu Thr Val Arg Val
1               5                   10                  15

Ile

<210> SEQ ID NO 71
<211> LENGTH: 16
<212> TYPE: PRT
<213> ORGANISM: Artificial Sequence
<220> FEATURE:
<223> OTHER INFORMATION: CD31 peptide

<400> SEQUENCE: 71

Asn His Ala Ser Ser Val Pro Arg Ser Lys Ile Leu Thr Val Arg Val
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: CD31 peptide
```

```
<400> SEQUENCE: 72

Asn His Ala Ser Ser Val Pro Arg Ser Lys Ile Leu Thr Val Arg
1               5                   10                  15

<210> SEQ ID NO 73
<211> LENGTH: 14
<212> TYPE: PRT
<213> ORGANISM: Artificial Sequence
<220> FEATURE:
<223> OTHER INFORMATION: CD31 peptide

<400> SEQUENCE: 73

Asn His Ala Ser Ser Val Pro Arg Ser Lys Ile Leu Thr Val
1               5                   10

<210> SEQ ID NO 74
<211> LENGTH: 13
<212> TYPE: PRT
<213> ORGANISM: Artificial Sequence
<220> FEATURE:
<223> OTHER INFORMATION: CD31 peptide

<400> SEQUENCE: 74

Asn His Ala Ser Ser Val Pro Arg Ser Lys Ile Leu Thr
1               5                   10

<210> SEQ ID NO 75
<211> LENGTH: 12
<212> TYPE: PRT
<213> ORGANISM: Artificial Sequence
<220> FEATURE:
<223> OTHER INFORMATION: CD31 peptide

<400> SEQUENCE: 75

Asn His Ala Ser Ser Val Pro Arg Ser Lys Ile Leu
1               5                   10

<210> SEQ ID NO 76
<211> LENGTH: 11
<212> TYPE: PRT
<213> ORGANISM: Artificial Sequence
<220> FEATURE:
<223> OTHER INFORMATION: CD31 peptide

<400> SEQUENCE: 76

Asn His Ala Ser Ser Val Pro Arg Ser Lys Ile
1               5                   10

<210> SEQ ID NO 77
<211> LENGTH: 10
<212> TYPE: PRT
<213> ORGANISM: Artificial Sequence
<220> FEATURE:
<223> OTHER INFORMATION: CD31 peptide

<400> SEQUENCE: 77

Asn His Ala Ser Ser Val Pro Arg Ser Lys
1               5                   10

<210> SEQ ID NO 78
<211> LENGTH: 9
<212> TYPE: PRT
<213> ORGANISM: Artificial Sequence
<220> FEATURE:
<223> OTHER INFORMATION: CD31 peptide

<400> SEQUENCE: 78
```

Asn His Ala Ser Ser Val Pro Arg Ser
1               5

<210> SEQ ID NO 79
<211> LENGTH: 8
<212> TYPE: PRT
<213> ORGANISM: Artificial Sequence
<220> FEATURE:
<223> OTHER INFORMATION: CD31 peptide

<400> SEQUENCE: 79

Asn His Ala Ser Ser Val Pro Arg
1               5

<210> SEQ ID NO 80
<211> LENGTH: 7
<212> TYPE: PRT
<213> ORGANISM: Artificial Sequence
<220> FEATURE:
<223> OTHER INFORMATION: CD31 peptide

<400> SEQUENCE: 80

Asn His Ala Ser Ser Val Pro
1               5

<210> SEQ ID NO 81
<211> LENGTH: 6
<212> TYPE: PRT
<213> ORGANISM: Artificial Sequence
<220> FEATURE:
<223> OTHER INFORMATION: CD31 peptide

<400> SEQUENCE: 81

Asn His Ala Ser Ser Val
1               5

<210> SEQ ID NO 82
<211> LENGTH: 5
<212> TYPE: PRT
<213> ORGANISM: Artificial Sequence
<220> FEATURE:
<223> OTHER INFORMATION: CD31 peptide

<400> SEQUENCE: 82

Asn His Ala Ser Ser
1               5

<210> SEQ ID NO 83
<211> LENGTH: 4
<212> TYPE: PRT
<213> ORGANISM: Artificial Sequence
<220> FEATURE:
<223> OTHER INFORMATION: CD31 peptide

<400> SEQUENCE: 83

Asn His Ala Ser
1

<210> SEQ ID NO 84
<211> LENGTH: 21
<212> TYPE: PRT
<213> ORGANISM: Artificial Sequence
<220> FEATURE:
<223> OTHER INFORMATION: CD31 peptide

<400> SEQUENCE: 84

```
Ser Met Arg Thr Ser Pro Arg Ser Ser Thr Leu Ala Val Arg Val Phe
1               5                   10                  15

Leu Ala Pro Trp Lys
            20

<210> SEQ ID NO 85
<211> LENGTH: 19
<212> TYPE: PRT
<213> ORGANISM: Artificial Sequence
<220> FEATURE:
<223> OTHER INFORMATION: CD31 peptide

<400> SEQUENCE: 85

Met Arg Thr Ser Pro Arg Ser Ser Thr Leu Ala Val Arg Val Phe Leu
1               5                   10                  15

Ala Pro Trp

<210> SEQ ID NO 86
<211> LENGTH: 17
<212> TYPE: PRT
<213> ORGANISM: Artificial Sequence
<220> FEATURE:
<223> OTHER INFORMATION: CD31 peptide

<400> SEQUENCE: 86

Arg Thr Ser Pro Arg Ser Ser Thr Leu Ala Val Arg Val Phe Leu Ala
1               5                   10                  15

Pro

<210> SEQ ID NO 87
<211> LENGTH: 15
<212> TYPE: PRT
<213> ORGANISM: Artificial Sequence
<220> FEATURE:
<223> OTHER INFORMATION: CD31 peptide

<400> SEQUENCE: 87

Thr Ser Pro Arg Ser Ser Thr Leu Ala Val Arg Val Phe Leu Ala
1               5                   10                  15

<210> SEQ ID NO 88
<211> LENGTH: 13
<212> TYPE: PRT
<213> ORGANISM: Artificial Sequence
<220> FEATURE:
<223> OTHER INFORMATION: CD31 peptide

<400> SEQUENCE: 88

Ser Pro Arg Ser Ser Thr Leu Ala Val Arg Val Phe Leu
1               5                   10

<210> SEQ ID NO 89
<211> LENGTH: 11
<212> TYPE: PRT
<213> ORGANISM: Artificial Sequence
<220> FEATURE:
<223> OTHER INFORMATION: CD31 peptide

<400> SEQUENCE: 89

Pro Arg Ser Ser Thr Leu Ala Val Arg Val Phe
1               5                   10

<210> SEQ ID NO 90
<211> LENGTH: 9
<212> TYPE: PRT
```

```
<213> ORGANISM: Artificial Sequence
<220> FEATURE:
<223> OTHER INFORMATION: CD31 peptide

<400> SEQUENCE: 90

Arg Ser Ser Thr Leu Ala Val Arg Val
1               5

<210> SEQ ID NO 91
<211> LENGTH: 7
<212> TYPE: PRT
<213> ORGANISM: Artificial Sequence
<220> FEATURE:
<223> OTHER INFORMATION: CD31 peptide

<400> SEQUENCE: 91

Ser Ser Thr Leu Ala Val Arg
1               5

<210> SEQ ID NO 92
<211> LENGTH: 5
<212> TYPE: PRT
<213> ORGANISM: Artificial Sequence
<220> FEATURE:
<223> OTHER INFORMATION: CD31 peptide

<400> SEQUENCE: 92

Ser Thr Leu Ala Val
1               5

<210> SEQ ID NO 93
<211> LENGTH: 21
<212> TYPE: PRT
<213> ORGANISM: Artificial Sequence
<220> FEATURE:
<223> OTHER INFORMATION: CD31 peptide

<400> SEQUENCE: 93

His Ala Ser Ser Val Pro Arg Ser Lys Ile Leu Thr Val Arg Val Ile
1               5                   10                  15

Leu Ala Pro Trp Lys
            20

<210> SEQ ID NO 94
<211> LENGTH: 19
<212> TYPE: PRT
<213> ORGANISM: Artificial Sequence
<220> FEATURE:
<223> OTHER INFORMATION: CD31 peptide

<400> SEQUENCE: 94

Ala Ser Ser Val Pro Arg Ser Lys Ile Leu Thr Val Arg Val Ile Leu
1               5                   10                  15

Ala Pro Trp

<210> SEQ ID NO 95
<211> LENGTH: 17
<212> TYPE: PRT
<213> ORGANISM: Artificial Sequence
<220> FEATURE:
<223> OTHER INFORMATION: CD31 peptide

<400> SEQUENCE: 95

Ser Ser Val Pro Arg Ser Lys Ile Leu Thr Val Arg Val Ile Leu Ala
1               5                   10                  15
```

Pro

<210> SEQ ID NO 96
<211> LENGTH: 15
<212> TYPE: PRT
<213> ORGANISM: Artificial Sequence
<220> FEATURE:
<223> OTHER INFORMATION: CD31 peptide

<400> SEQUENCE: 96

Ser Val Pro Arg Ser Lys Ile Leu Thr Val Arg Val Ile Leu Ala
1               5                   10                  15

<210> SEQ ID NO 97
<211> LENGTH: 13
<212> TYPE: PRT
<213> ORGANISM: Artificial Sequence
<220> FEATURE:
<223> OTHER INFORMATION: CD31 peptide

<400> SEQUENCE: 97

Val Pro Arg Ser Lys Ile Leu Thr Val Arg Val Ile Leu
1               5                   10

<210> SEQ ID NO 98
<211> LENGTH: 11
<212> TYPE: PRT
<213> ORGANISM: Artificial Sequence
<220> FEATURE:
<223> OTHER INFORMATION: CD31 peptide

<400> SEQUENCE: 98

Pro Arg Ser Lys Ile Leu Thr Val Arg Val Ile
1               5                   10

<210> SEQ ID NO 99
<211> LENGTH: 9
<212> TYPE: PRT
<213> ORGANISM: Artificial Sequence
<220> FEATURE:
<223> OTHER INFORMATION: CD31 peptide

<400> SEQUENCE: 99

Arg Ser Lys Ile Leu Thr Val Arg Val
1               5

<210> SEQ ID NO 100
<211> LENGTH: 7
<212> TYPE: PRT
<213> ORGANISM: Artificial Sequence
<220> FEATURE:
<223> OTHER INFORMATION: CD31 peptide

<400> SEQUENCE: 100

Ser Lys Ile Leu Thr Val Arg
1               5

<210> SEQ ID NO 101
<211> LENGTH: 5
<212> TYPE: PRT

```
<213> ORGANISM: Artificial Sequence
<220> FEATURE:
<223> OTHER INFORMATION: CD31 peptide

<400> SEQUENCE: 101

Lys Ile Leu Thr Val
1               5
```